United States Patent [19]

Murray et al.

[11] Patent Number: 5,665,557
[45] Date of Patent: Sep. 9, 1997

[54] METHOD OF PURIFYING A POPULATION OF CELLS ENRICHED FOR HEMATOPOIETIC STEM CELLS POPULATIONS OF CELLS OBTAINED THEREBY AND METHODS OF USE THEREOF

[75] Inventors: Lesley Murray, San Jose, Calif.; D. Robert Sutherland, Oakville, Canada

[73] Assignees: Systemix, Inc., Palo Alto, Calif.; The Toronto Hospital Research Institute, Toronto, Canada

[21] Appl. No.: 340,048

[22] Filed: Nov. 14, 1994

[51] Int. Cl.$^6$ .................. C12N 5/08; C12Q 1/24
[52] U.S. Cl. .................. 435/7.24; 435/2; 435/30; 435/378; 435/372
[58] Field of Search .................. 435/2, 7.24, 30, 435/240.2

[56] References Cited

U.S. PATENT DOCUMENTS

| | | | |
|---|---|---|---|
| 4,714,680 | 12/1987 | Civin | 435/240.25 |
| 5,061,620 | 10/1991 | Tsukamoto et al. | 435/7.21 |
| 5,147,784 | 9/1992 | Peault | 435/7.24 |
| 5,464,753 | 11/1995 | Chaudhary et al. | 435/7.24 |

FOREIGN PATENT DOCUMENTS

0341966  11/1989  European Pat. Off. .

OTHER PUBLICATIONS

Baum et al. "Isolation of a candidate human hematopoietic stem–cell population" *Proc. Natl. Acad. Sci. USA* (1992) 89:2804–2808.

Spangrude et al. "Purification and characterization of mouse hematopoietic stem cells" *Science* (1988) 241:58–62.

Smith et al. "Clonal analysis of hematopoietic stem–cell differentiation in vivo" *Proc. Natl. Acad. Sci. USA* (1991) 88:2788–2792.

Uchida, Dialog™ Dissertation Abstract *Ph.D. Thesis* (1992) Stanford University, 2 pages total.

Sutherland et al., "Identification of a cell–surface antigen associated with activated T lymphoblasts and activated platelets" *Blood* (1991) 77:84–93.

DiGiusto et al., "Human fetal bone marrow early progenitors for T, B, and myeloid cells are found exclusively in the population expressing high levels of CD34" *Blood* (1994) 84:421–432.

Whitlock et al., "Long–term culture of B lymphocytes and their precursors from murine bone marrow" *Proc. Natl. Acad. Sci. USA* (1982) 79:3608–3612.

Whitlock et al., "Bone marrow stromal cell lines with lymphopoietic activity express high levels of a pre–B neoplasia–associated molecule" *Cell* (1987) 48:1009–1021.

Spangrude, "Enrichment of murine haemopoietic stem cells: diverging roads" *Immunol. Today* (1989) 10:344–350.

Haugland, *Handbook of Fluorescent Probes and Research Chemicals*, Larison, K.D., ed., 5th ed., Molecular Probes, Inc., (1992). The title page and table of contents are included herewith.

Kyoizumi et al., "Implantation and maintenance of functional human bone marrow in SCID–hu mice" *Blood* (1992) 79:1704–1711.

Metcalf, *Hemopoietic Colonies. In vitro Cloning of Normal and Leukemic Cells*, (1977) Springer–Verlag, Germany. The title page and table of contents are included herewith.

Sambrook et al., *Molecular Cloning A Laboratory Manual*, 2nd ed., (1989) Cold Spring Harbor Laboratory Press, New York. The title page and table of contents are included herewith.

Marsh et al., "Retention of progenitor cell function in CD34$^+$ cells purified using a novel O–sialoglycoprotease" *Leukemia* (1992) 6:926–934.

Brandt et al., "Role of c–kit ligand in the expansion of human hematopoietic progenitor cells" *Blood* (1992) 79:634–641.

Bruno et al., "Effect of recombinant and purified hematopoietic growth factors on human megakaryocyte colony formation" *Exp. Hematol.* (1988) 16:371–377.

Bruno et al., "Interacting cytokines regulate in vitro human megakaryocytopoiesis" *Blood* (1989) 73:671–677.

Briddell et al., "Characterization of the human burst–forming unit–megakaryocyte" *Blood* (1989) 74:145–151.

de Sauvage et al., "Stimulation of megakaryocytopoiesis and thrombopoiesis by the c–Mpl ligand" *Nature* (1994) 369:533–538.

Kaushansky et al., "Promotion of megakaryocyte progenitor expansion and differentiation by the c–Mpl ligand thrombopoietin" *Nature* (1994) 369:568–571.

Wendling et al., "c–Mpl ligand is a humoral regulator of megakaryocytopoiesis" *Nature* (1994) 369:571–574.

Bartley et al., "Identification and cloning of a megakaryocyte growth and development factor that is a ligand for the cytokine receptor Mpl" *Cell* (1994) 77:1117–1124.

Lefkovits et al., "Limiting dilution analysis of the cells of immune system. I. The clonal basis of the immune response" *Immunol. Today* (1984) 5:265–268.

Schneider et al., "A one–step purification of membrane proteins using a high efficiency immunomatrix" *J. Biol. Chem.* (1982) 257:10766–10769.

Sutherland et al., "Sensitive detection and enumeration of CD34$^+$ cells in peripheral and cord blood by flow cytometry" *Exp. Hematol.* (1994) 22:1003–1010.

Yeo et al "CDw109: A Novel Platelet and Endothelial Cell Actuation Specific Antigen", Abstract No. 19 Published in Conjunction with 1994 Canadian Red Cross Scientific Meeting, Chateau Whistler, British Columbia (Apr. 23–26, 1994).

(List continued on next page.)

*Primary Examiner*—David Saunders
*Attorney, Agent, or Firm*—Morrison & Foerster LLP

[57] ABSTRACT

The invention relates to methods of obtaining compositions enriched in hematopoietic stem cells by separating out an enriched fraction of cells expressing the marker CDw109. Methods of obtaining compositions enriched in hematopoietic megakaryocyte progenitor cells are also provided. Compositions enriched for stem cells and populations of cells obtained therefrom are also provided by the invention. Methods of use of the cells are also included.

21 Claims, 12 Drawing Sheets

OTHER PUBLICATIONS

Yeo, et al. "A Benard–Soulier–Like Defect: Selective Cleavage of GPbα with a Novel O–Sialoglycoprotein Endopeptidase" Abstract No. 31 published in conjuction with 1994 Canadian Red Cross Scientific Meeting, Chateau Whistler, British Columbia (Apr. 23–26, 1994).

Farley et al. "Divergem Molecular Phenotypes of KG1 and KG1 a Myeloid Cell Lines" (1986) Blood Vol 68(5):1101–1107.

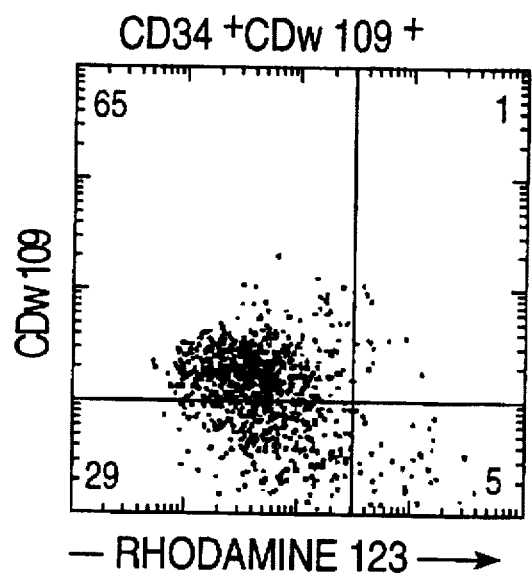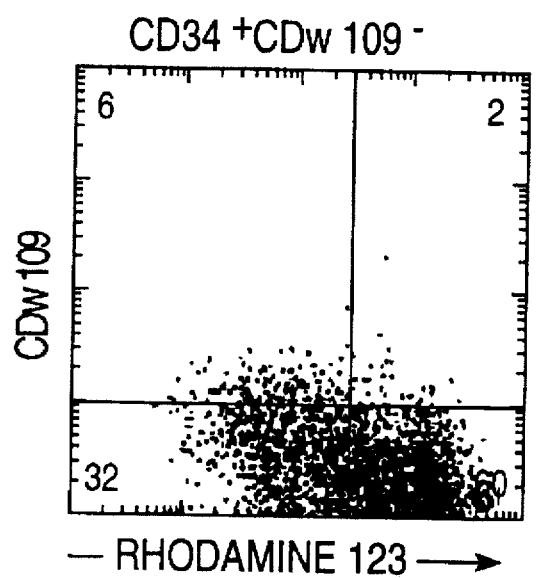
FIG. 5A  FIG. 5B

METHOD OF PURIFYING A POPULATION OF CELLS ENRICHED FOR HEMATOPOIETIC STEM CELLS POPULATIONS OF CELLS OBTAINED THEREBY AND METHODS OF USE THEREOF

FIELD OF THE INVENTION

The invention relates to methods of purifying hematopoietic cell populations enriched in hematopoietic stem cells based on a cell specific marker. The methods also provide an enriched population of these stem cells. Compositions enriched for the cells and populations of cells obtained therefrom are also provided by the invention. Methods of use of the cells are also included.

BACKGROUND OF THE INVENTION

Mammalian hematopoietic cells provide a diverse range of physiologic activities. These cells are divided into lymphoid, myeloid and erythroid lineages. The lymphoid lineage, comprising B cells and T cells, provides for the production of antibodies, regulation of the cellular immune system, detection of foreign agents in the blood, detection of cells foreign to the host, and the like. The myeloid lineage, which includes monocytes, granulocytes, megakaryocytes, as well as other cells, monitors for the presence of foreign bodies, provides protection against neoplastic cells, scavenges foreign materials, and produces platelets, and the like. The erythroid lineage provides the red blood cells, which act as oxygen carriers.

All publications cited herein are hereby incorporated herein by reference in their entirety.

Despite the diversity of the nature, morphology, characteristics and function of hematopoietic cells, it is presently believed that these cells are derived from a single cell population, termed "stem cells." Unlike more "mature" blood cells, stem cells are capable of self-regeneration but may also divide into progenitor cells that are no longer pluripotent and capable of self-regeneration. These progenitor cells divide repeatedly to form more mature cells which eventually become terminally differentiated to form the various mature hematopoietic cells. Thus the large number of mature hematopoietic cells is derived from a small reservoir of stem cells by a process of proliferation and differentiation. As used herein, "stem cells" refers to hematopoietic stem cells and not stem cells of other cell types.

Stem cells mature into progenitor cells and then become lineage committed, that is, are incapable of maturing into all of the lineages. The use of the words progenitor or progenitor cells indicates cell populations which are no longer stem cells but which have not yet become terminally differentiated. The use of the word lymphoid, myeloid or erythroid in conjunction with progenitor indicates the potential cell populations into which the progenitor is capable of maturing.

Highly purified populations of stem cells currently find use in long-term repopulation of the entire hematopoietic system. Purified progenitor cells of individual lineages would find use only in transiently repopulating or augmenting the various lineages. As progenitors are not believed to be self-regenerating, the repopulation or augmentation would be limited, for example, to short-term hematopoietic reconstitution.

A highly purified or enriched population of stem cells is necessary for a variety of in vitro experiments and in vivo indications. For instance, a purified population of stem cells will allow for identification of growth factors associated with their self-regeneration. In addition, there may be as yet undiscovered growth factors associated with: (1) the early steps of dedication of the stem cell to a particular lineage; (2) the prevention of such dedication; and (3) the negative control of stem cell proliferation.

Stem cells find use in: (1) regenerating the hematopoietic system of a host deficient in any class of hematopoietic cells; (2) a host that is diseased and can be treated by removal of bone marrow, isolation of stem cells and treatment with drugs or irradiation prior to re-engraftment of stem cells; (3) producing various hematopoietic cells; (4) detecting and evaluating growth factors relevant to stem cell self-regeneration; and (5) the development of hematopoietic cell lineages and assaying for factors associated with hematopoietic development.

Stem cells are also important targets for gene therapy, where expression of the inserted genes promotes the health of the individual into whom the stem cells are transplanted. In addition, the ability to isolate stem cells may serve in the treatment of lymphomas and leukemias, as well as other neoplastic conditions where the stem cells are purified from tumor cells in the bone marrow or peripheral blood, and reinfused into a patient after myelosuppressive or myeloablative chemotherapy. Thus, there have been world-wide efforts toward isolating stem cells in substantially pure or pure form.

Stem cells and progenitor cells constitute only a small percentage of the total number of hematopoietic cells. Hematopoietic cells are identifiable by the presence of a variety of cell surface protein or carbohydrate "markers." Such markers may be either specific to a particular lineage or be present on more than one cell type. The markers also change with stages of differentiation. Currently, it is not known how many of the markers associated with differentiated cells are also present on stem and progenitor cells. One marker which was previously indicated as present solely on stem cells, CD34, raised against KG1a cells, is also found on a significant number of lineage committed progenitors. U.S. Pat. No. 4,714,680 describes a composition comprising human CD34$^+$ stem and progenitor cells.

The CD34 marker is found on numerous lineage committed hematopoietic cells. In particular, 80–90% of the CD34$^+$ population is marked by other lineage specific and non-specific markers. In view of the small proportion of the total number of cells in the bone marrow or peripheral blood which are stem cells, the uncertainty of the markers associated with the stem cell as distinct from more differentiated cells, and the general difficulty in assaying for human stem cells biologically, the identification and purification of stem cells has been elusive. Characterizations and isolation of human stem cells are reported in: Baum et al. (1992) *Proc. Natl. Acad. Sci. USA* 89:2804–2808; and Tsukamoto et al. U.S. Pat. No. 5,061,620.

Recently, the mouse stem cell has been obtained in at least highly concentrated, if not a purified form, where fewer than about 30 cells obtained from bone marrow were able to reconstitute all of the lineages of the hematopoietic system of a lethally irradiated mouse. Each assayed cell is multipotent for all hematopoietic lineages, while self-renewal is variable amongst these cells. Spangrude et al. (1988) *Science* 241:58–62; Smith et al. (1991) *Proc. Natl. Acad. Sci. USA* 88:2788–2792; Uchida (1992) *Ph.D. Thesis* Stanford U.; and see also, EPA 89 304651.6 and the references cited therein which describe the isolation of mouse stem cells.

The cell surface marker CDw109, a monomeric GPI-linked glycoprotein of 170 kD has been found to be expressed on primitive T-lymphoblastic leukemias, activated platelets and activated T-lymphoblasts while they are maintained in IL-2. Sutherland et al. (1991) *Blood* 77:84–93. CDw109 was reported to be unexpressed on whole bone marrow or peripheral blood lymphocytes.

SUMMARY OF THE INVENTION

The present invention provides methods of obtaining compositions enriched for stem cells. The methods comprise isolating a population of hematopoietic cells and purifying those cells expressing the cell surface marker CDw109. The invention also encompasses compositions obtained thereby and methods of use thereof.

BRIEF DESCRIPTION OF THE DRAWINGS

FIG. 1A depicts the isotype control. FIG. 1B depicts the CD34$^+$ cells stained for CDw109 expression. FIG. 1C depicts the reanalysis of CD34$^+$ cells that are CDw109$^-$. FIG. 1D depicts the reanalysis of CD34$^+$ cells that are CDw109$^+$. FIG. 1E depicts the scatter profile of CDw109$^-$ cells. FIG. 1F depicts the scatter profile of CDw109$^+$ cells.

FIG. 2A shows FACS analysis of FBM cells for CD34 and CDw109 expression. Region "R3" represents cells which are CD34$^{hi}$ and CDw109$^+$. FIG. 2B shows reanalysis of CD34$^{lo}$CDw109$^-$ cells for CD38 expression. FIG. 2C depicts reanalysis of CD34$^{hi}$CDw109$^{30}$ cells for CD38 expression.

FIG. 3A depicts analysis of CD34$^{30}$ cells for both CDw109 rho123 expression. FIG. 3B shows analysis of CD34$^+$ cells for Thy-1 and rho-123 expression. FIGS. 3C and 3D depict analysis of CD34$^+$rho123$^{lo}$ cells for Thy-1 and CDw109 expression.

FIGS. 4A–4C show analysis of rho123$^{lo}$ cells for CD34, CDw109 (FIG. 4B) and Thy-1 (FIG. 4C) expression. FIGS. 4D through 4F show reanalysis of rho123$^{lo}$CD34$^{+ =l\ cells\ for\ CDw}$109 (FIG. 4E) and Thy-1 (FIG. 4F) expression.

FIGS. 5 (A and B) show the reanalysis of sorted ABM CD34$^+$ subpopulations separated by CDw109.

FIG. 6A shows FACS fluorescence analysis of KG1a cells incubated with biotinylated 8A3 antibody. FIG. 6B depicts fluorescence when KG1a cells are incubated with biotinylated 8A3 and 7D1 antibodies. FIG. 6C shows incubation with 8A3, 7D1 antibodies. FIG. 6D depicts fluorescence with 8A3, 7D1, 7D1, 8A1 and 40B8 antibodies. FIG 6E shows fluorescence with 8A3, 7D1, 8A1, 40B8 and 7C5 antibodies. FIG. 6F shows the forward scatter and side scatter profiles of CDw109$^+$ cells.

FIGS 7A and 7B depict two groups (R1 and R2) of ABM MNC cells selected for staining.

FIG. 7N shows staining in R1, R2, R3 and R6 cells.

DETAILED DESCRIPTION OF THE INVENTION

Figure 1A:
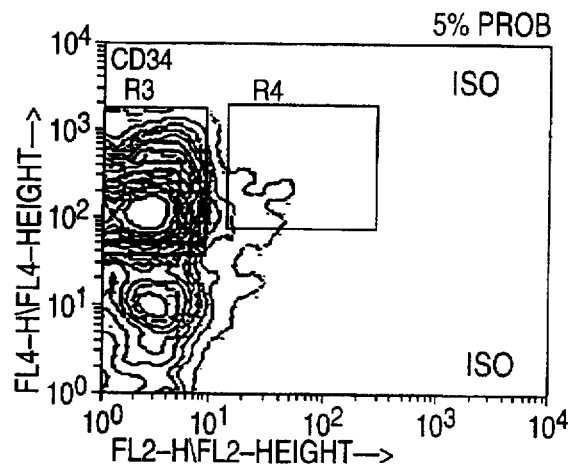
FIGS. 1A–1F show FACS analyses of fetal bone marrow (FBM) cells (S069) sorted with respect to various parameters.
Figure 1B:
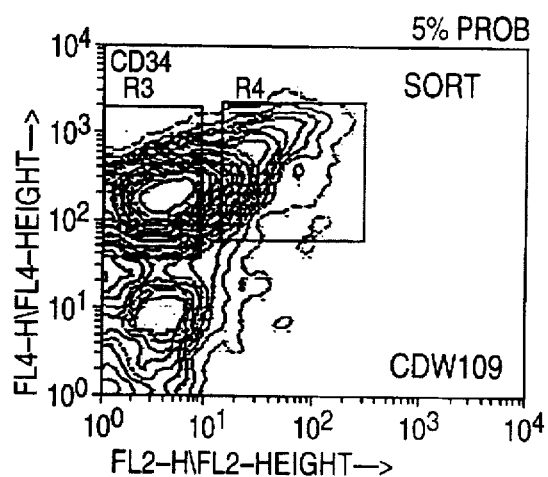
Figure 1C:
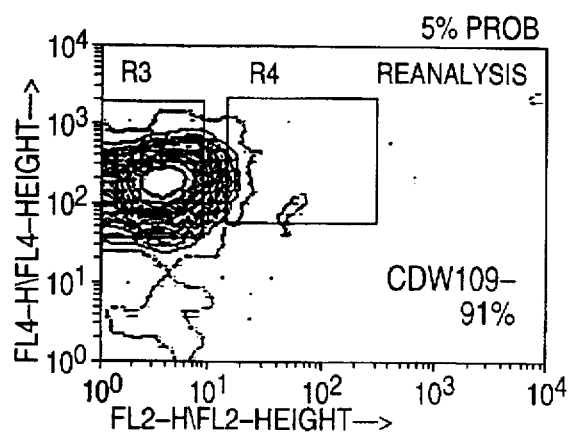
Figure 1D:
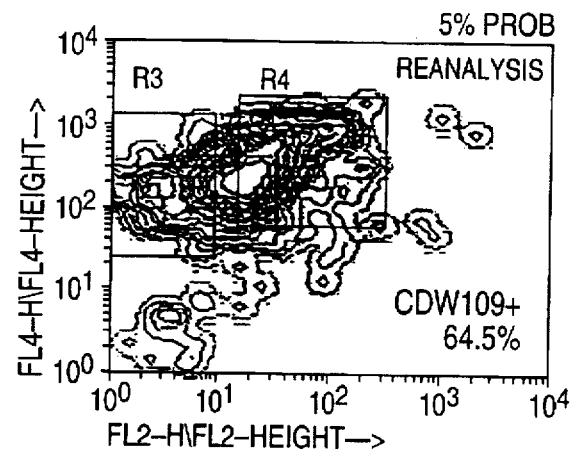
Figure 1E:
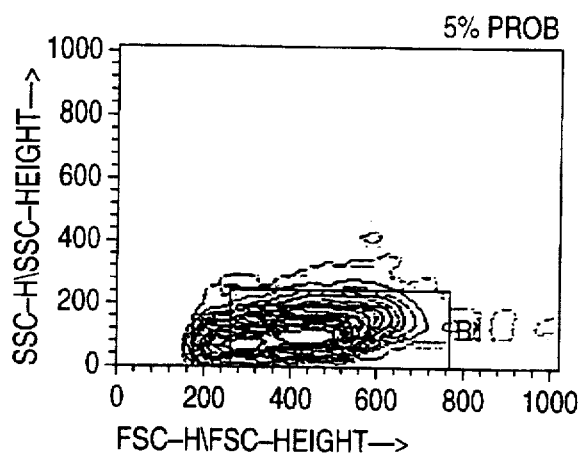
Figure 1F:
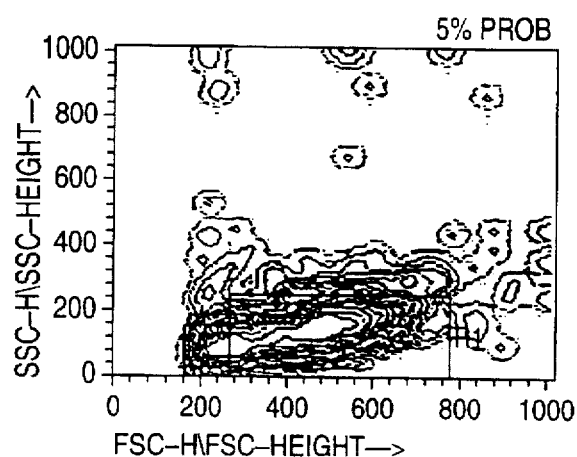

The invention utilizes antibodies specific for CDw109. As used herein, the term "αCDw109 antibody" encompasses all such antibodies. As used herein, "αCDw109 antibody" encompasses any antibody or fragment thereof, both native and recombinant, which retains sufficient specificity to bind specifically to CDw109. "8A3" is a αCDw109 antibody in the examples provided herein. All other antibodies tested for specificity to CDw109, however, have been found to be suitable for the practice of the present invention.

The results presented herein indicate that αCDw109 antibodies recognize and bind with high specificity a small subpopulation of primitive hematopoietic cells including stem and some progenitor cells. This specificity can be used to isolate and purify these stem and progenitor cells to obtain compositions enriched for these cells.

As used herein, "CDw109" refers to the hematopoietic marker that carries the epitope recognized by monoclonal antibody 8A3. As used herein, CDw109$^+$ cells refer to those cells expressing a marker recognized by monoclonal antibodies 8A3, 7D1, 7C5, 8A1 or any antibody whether monoclonal or polyclonal which binds to the molecule that carries the epitopes recognized by these antibodies. This also includes any antibody having the same antigenic specificity as these antibodies.

Samples of the hybridoma cell line which produce antibody 8A3 were deposited with the American Type Culture Collection (ATCC), 12301 Parklawn Drive, Rockville, Md. 20852, U.S.A. on Nov. 14, 1996 under the provisions of the Budapest Treaty on the Internationl Recognition of the Deposit of Microorganisms for the Purposes of Patent Procedure and accorded ATCC Accession Number HB-12237.

αCDw109 antibodies are obtained by any method known in the art for monoclonal antibody production. The actual methods used are described in Sutherland et al. (1991) utilizing the cell line KG1a, although any method known in the art of antibody production may be used. Such methods include, but are not limited to, inoculating animals with cells expressing CDw109, the purified protein or portions thereof whether enzymatically obtained from purified proteins or recombinant or synthetic fragments; separating B cells with cell-surface antibodies of the desired specificity from the animal, cloning the DNA expressing the variable regions of the light and heavy chains and expressing the recombinant genes in a suitable host cell. Standard monoclonal antibody generation techniques can be used wherein the antibodies are obtained from immortalized antibody-producing hybridoma cells. These hybridomas can be produced by immunizing animals with stem cells, purified CDw109 protein or antigenic portions thereof, and fusing B lymphocytes from the immunized animals, preferably isolated from the immunized host spleen, with compatible immortalized cells, preferably a B cell myeloma.

It has now been found that cells that are recognized by αCDw109 antibodies are enriched for stem cells and myeloid/megakaryocytic/erythroid progenitors. In fetal bone marrow (FBM), 8A3 identified a mean of 13.4% of CD34$^+$ cells that included almost all the FBM CD34$^{hi}$ subset, suggesting that this antigen might be expressed by the most primitive pluripotential hematopoietic stem cells (PHSCs). CD34$^{hi}$ refers to CD34$^+$ cells which have at least 100 times CD34 antigen density compared to isotype controls. DiGiusto et al. (1994) *Blood* 84:421, 1994.

In particular, it has been found that the CDw109$^+$ subset of CD34$^+$ cells contains virtually all stem cells and megakaryocyte progenitor activity as well as myeloid and erythroid progenitor cells, but appears to lack lymphoid progenitor activity. These characteristics make the CD34$^+$CDw109$^+$ cell population particularly attractive for use in an allogeneic transplant setting. A CD34$^+$CDw109$^+$ cell population will provide not only stem cells for long-term hematopoietic recovery but also progenitor cells that may aid in short-term hematopoietic reconstitution, while the depletion of lymphoid progenitors will avoid graft-versus-host problems associated with allogeneic transplants. In addition, depletion of lymphoid progenitors should avoid the emergence of EBV-transformed B-cell lymphomas seen in some transplant settings.

Since the CDw109$^+$ subset of CD34$^+$ cells also contains all the megakaryocyte progenitor activity, this population can be used to expand megakaryocyte progenitors, for example, using the Mp1-ligand as described in the Examples herein. Such a population would be useful in providing for platelet recovery in a depleted host.

As used herein, Lin$^-$ cells generally refer to cells which lack markers associated with T cells (such as CD2, 3, 4 and 8), B cells (such as CD10, 19 and 20), myeloid cells (such as CD14, 15, 16 and 33), natural killer ("NK") cells (such as CD2, 16 and 56), RBC (such as glycophorin A), megakaryocytes, mast cells, eosinophils or basophils. The absence or low expression of such lineage specific markers is identified by the lack of binding of antibodies specific to the cell specific markers, useful in so-called "negative selection". Analyses for hematopoietic progenitors have been reported by Whitlock and Witte (1982) *Proc. Natl. Acad. Sci. USA* 79:3608–3612; and Whitlock et al. (1987) *Cell* 48:1009–1021.

In addition to being recognized by αCDw109 antibodies, the stem cells described herein may be characterized by the following phenotypes. In the case of fetal cells including, but not limited to: CD34$^+$, CD34$^{hi}$, CD3$^-$, CD7$^-$, CD8$^-$, CD10$^-$, CD14$^-$, CD15$^-$, CD19$^-$, CD20$^-$, and Thy-1$^+$. In the case of adult cells including, but not limited to: CD34$^+$, CD34$^{hi}$, CD3$^-$, CD7$^-$, CD8$^-$, CD10$^-$, CD14$^-$, CD15$^-$, CD19$^-$, CD20$^-$, and Thy-1$^+$ or as represented in Table 1. Also, rho123 can divide the cells into high and low subsets ("rho$^{lo}$" and "rho$^{hi}$"). See Spangrude (1989) *Immunol. Today* 10:344–350, for a description of the use of rho123 with mouse stem cells. Preferably the cells are rho$^{lo}$. Preferably, the CDw109$^+$ cells are human but may derive from any suitable animal.

Table 1 summarizes probable phenotypes of stem cells in fetal, adult, and mobilized peripheral blood. In Table 1 myelomonocytic stands for myelomonocytic associated markers, NK stands for natural killer cells and AMPB stands for adult mobilized peripheral blood. As used herein both infra, supra and in Table 1, the negative sign or, uppercase negative sign, (−) means that the level of the specified marker is undetectable above Ig isotype controls by FACS analysis, and includes cells with very low expression of the specified marker.

TABLE 1

| | Probable Stem Cell Phenotypes | | | | | | | | | | | | | | | |
|---|---|---|---|---|---|---|---|---|---|---|---|---|---|---|---|---|
| | NK and T cell markers | | | B cell markers | | | Myelomonocytic | | | Other | | | | | | |
| | | | | | | | | | | | | | HLA- | | | P-gp |
| | CD2 | CD3 | CD8 | CD10 | CD19 | CD20 | CD14 | CD15 | CD16 | CD33 | CD34 | CD38 | DR | C-Kit | Thy | Rho | Activity |
| FBM | − | − | − | − | − | − | − | − | − | ? | + | − | + | + | + | lo | + |
| ABM | − | − | − | − | − | − | − | − | − | − | + | − | lo/− | + | + | lo | + |
| AMPB | − | − | − | − | − | − | − | − | − | lo/−? | + | ? | lo/− | ? | + | lo | + |

In one embodiment, the present invention is directed to methods for obtaining cell compositions enriched for stem cells. Sources of cells for subsequent purification include, but are not limited to, bone marrow, both adult and fetal, mobilized peripheral blood (MPB), blood, umbilical cord blood, embryonic yolk sac, fetal liver, and spleen, both adult and fetal. Bone marrow cells may be obtained from any known source, including but not limited to, ilium (e.g. from the hip bone via the iliac crest), sternum, tibiae, femora, spine, or other bone cavities.

For isolation of bone marrow from fetal bone or other bone source, an appropriate solution may be used to flush the bone, including but not limited to, salt solution, conveniently supplemented with fetal calf serum (FCS) or other naturally occurring factors, in conjunction with an acceptable buffer at low concentration, generally from about 5–25 mM. Convenient buffers include, but are not limited to, Hepes, phosphate buffers and lactate buffers. Otherwise, bone marrow may be aspirated from the bone in accordance with conventional techniques.

Selection of the stem cells need not be achieved solely with a marker specific for the cells. By using a combination of negative selection and positive selection, enriched cell populations can be obtained.

Various techniques may be employed to separate the cells by initially removing cells of dedicated lineage. Monoclonal antibodies are particularly useful for identifying markers associated with particular cell lineages and/or stages of differentiation. The antibodies may be attached to a solid support to allow for crude separation. The separation techniques employed should maximize the retention of viability of the fraction to be collected. Various techniques of different efficacy may be employed to obtain "relatively crude"

separations. Such separations are where up to 10%, usually not more than about 5%, preferably not more than about 1%, of the total cells present are undesired cells that remain with the cell population to be retained. The particular technique employed will depend upon efficiency of separation, associated cytotoxicity, ease and speed of performance, and necessity for sophisticated equipment and/or technical skill.

Procedures for separation may include but are not limited to, magnetic separation using antibody-coated magnetic beads; affinity chromatography; cytotoxic agents joined to a monoclonal antibody or used in conjunction with a monoclonal antibody, including but not limited to, complement and cytotoxins; and "panning" with antibody attached to a solid matrix, e.g., plate, or any other convenient technique.

The use of separation techniques include, but are not limited to, those based on differences in physical (density gradient centrifugation and counter-flow centrifugal elutriation), cell surface (lectin and antibody affinity), and vital staining properties (mitochondria-binding dye rho123 and DNA-binding dye Hoechst 33342).

Techniques providing accurate separation include but are not limited to, FACS, which can have varying degrees of sophistication, e.g., a plurality of color channels, low angle and obtuse light scattering detecting channels, impedance channels, etc.

The antibodies can be conjugated to identifiable agents including, but not limited to, enzymes, magnetic beads, colloidal magnetic beads, haptens, fluorochromes, metal compounds, radioactive compounds, drugs or haptens. The enzymes that can be conjugated to the antibodies include, but are not limited to, alkaline phosphatase, peroxidase, urease and β-galactosidase. The fluorochromes that can be conjugated to the antibodies include, but are not limited to, fluorescein isothiocyanate, tetramethylrhodamine isothiocyanate, phycoerythrin, allophycocyanins and Texas Red. For additional fluorochromes that can be conjugated to antibodies, see Haugland, *Molecular Probes: Handbook of Fluorescent Probes and Research Chemicals* (1992–1994). The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxygenin, oxazalone, and nitrophenol. The radioactive compounds that can be conjugated or incorporated into the antibodies are known to the art, and include but are not limited to technetium 99 m ($^{99}$TC), $^{125}$I and amino acids comprising any radionuclides, including, but not limited to, $^{14}$C, $^{3}$H and $^{35}$S.

Other techniques for positive selection may be employed, which permit accurate separation, such as affinity columns, and the like. The method should permit the removal to a residual amount of less than about 20%, preferably less than about 5%, of the non-target cell populations.

Cells may be selected based on light-scatter properties as well as their expression of various cell surface antigens. The purified stem cells have low side scatter and low to medium forward scatter profiles by FACS analysis. Cytospin preparations show the enriched stem cells to have a size between mature lymphoid cells and mature granulocytes.

While it is believed that the particular order of separation is not critical to this invention, the order indicated is preferred. Preferably, cells are initially separated by a coarse separation, followed by a fine separation, with positive selection of one or more markers associated with the stem cells and negative selection for markers associated with lineage committed cells.

The enriched stem cell population is identified by being CDw109$^+$ and/or Lin$^-$; and/or Thy-1$^+$; and/or CD34$^+$; and/or rho$^{lo}$, or combinations of these markers as listed in Table 2, and being able to provide for cell regeneration and development of members of all of the various hematopoietic lineages. Note that the blank spaces in Table 2 do not mean that the cells are negative for the specified marker; they simply mean the marker is not used.

TABLE 2

Possible Combinations of Selections for Stem Cell Populations

| CDw109$^+$ | CD34$^+$ | Thy$^+$ | Lin$^-$ | rho$^{lo}$ |
|---|---|---|---|---|
| + | + | + | + | + |
| + | + | + | + |   |
| + | + | + |   |   |
| + | + |   |   |   |
| + | + |   |   | + |
| + |   | + |   | + |
| + |   | + | + | + |
| + |   |   | + | + |
| + |   |   | + |   |
|   | + | + | + |   |
|   | + | + | + | + |
|   |   | + | + | + |
|   | + |   | + | + |
|   |   |   |   | + |

The cells obtained as described above and in the Examples may be used immediately or frozen at liquid nitrogen temperatures and stored for long periods of time, being thawed and capable of being reused. The cells will usually be stored in 10% DMSO, 50% FCS, 40% RPMI 1640 medium. Once thawed, the cells may be expanded by use of growth factors or stromal cells associated with proliferation and differentiation.

By separating CDw109$^+$ cells from human hematopoietic sources, either in combination with another positively selected marker such as CD34, or in combination with a negative selection for lineage-specific markers, the long-term culture activity is enriched in the CDw109$^+$ fraction compared to the CDw109$^-$ fraction. Moreover, the CDw109$^+$ cells will generate both B and myeloid cells in long-term cultures and contain virtually all of the megakaryocyte potential. In further enrichments of the CDw109$^+$ cells using antibodies to Thy-1 and/or any of the combinations specified in Table 2 and/or c-kit, the stem cell frequency can be further increased.

The separated cells will generally be fewer than 5% of the original cells, generally in the range of 1% or fewer; for example, when combined with CD34$^+$ selection, CD34$^+$ CDw109$^+$ cells represent approximately 1% of the cells in whole bone marrow. By using additional negative selection for lineage-specific markers, the frequency of stem cells and if desired, certain progenitors (e.g. megakaryocyte) can be further increased.

The cells generated from CDw109$^+$ cells and obtained from these cultures can give rise to B cells, T cells and myelomonocytic cells in the in vivo assays described below.

A pluripotent stem cell may be defined as follows: (1) gives rise to progeny in all defined hematolymphoid lineages; and (2) limiting numbers of cells are capable of fully reconstituting a seriously immunocompromised human host, or animal model thereof, in all blood cell types and their progenitors, including the pluripotent hematopoietic stem cell by self-renewal.

To demonstrate differentiation to T cells, fetal thymus is isolated and cultured for from 4–7 days at about 25° C., so as to deplete substantially the lymphoid population. The cells to be tested for T cell activity are then microinjected into the thymus tissue, where the HLA of the population which is injected is mismatched with the HLA of the thymus cells. The thymus tissue may then be transplanted into a scid/scid mouse as described in U.S. Pat. No. 5,147,784, particularly transplanting under the kidney capsule.

Specifically, the sorted population enriched for stem cells (or the control, lacking stem cells,) can be microinjected into HLA mismatched thymus fragments. After 6–10 weeks, assays of the thymus fragments injected with the CDw109$^+$ cells can be performed and assessed for donor derived T cells. Thymus fragments injected with the CDw109$^+$ cells will generate and sustain CD3$^+$, CD4$^+$, and CD8$^+$ T cells along with their progenitors. Subfractionation of the CDw109$^+$ fraction based on Thy$^+$ and/or Lin$^-$ and/or c-kit and/or rho123 should demonstrate enrichment of activity.

Further demonstration of the sustained ability of the various cell populations may be accomplished by the detection of continued myeloid and B-lymphoid cell production in the SCID-hu bone model. Kyoizumi et al. (1992) *Blood* 79:1704. To analyze this, one may isolate human fetal bone and transfer a longitudinally sliced portion of this bone under the skin of a scid/scid animal: the bone cavity is diminished of endogenous cells by whole body irradiation of the mouse host prior to infection of the test donor population. The HLA of the population which is injected is mismatched with the HLA of the host bone cells. CDw109$^+$ cells from human hematopoietic sources will sustain B lymphopoiesis and myelopoiesis in the SCID-hu bone model.

For RBCs, one may use conventional techniques to identify BFU-E units, for example methylcellulose culture demonstrating that the cells are capable of developing the erythroid lineage. Metcalf (1977) In: Recent Results in Cancer Research 61. Springer-Verlag, Berlin, pp. 1–227.

Once the CDw109$^+$ cells have been isolated, they may be propagated on stromal cells, such as stromal cells that can be obtained from bone marrow, fetal thymus or fetal liver, and are shown to provide for the secretion of growth factors associated with progenitor cell maintenance where the stromal cells may be allogeneic or xenogeneic. Before using in the co-culture, the mixed stromal cell preparations may be freed of hematopoietic cells employing appropriate monoclonal antibodies for removal of the undesired cells, e.g., with antibody-toxin conjugates, antibody and complement, etc. Alternatively, cloned stromal cell lines may be used where the stromal lines may be allogeneic or xenogeneic.

The invention also encompasses methods of use of the CDw109$^+$ cell populations. The subject cell compositions may find use in any method known in the art. Since the cells are naive, they can be used to fully reconstitute an immunocompromised host such as an irradiated host or a host subject to chemotherapy; or as a source of cells for specific lineages, by providing for their maturation, proliferation and differentiation into one or more selected lineages by employing a variety of factors, including, but not limited to, erythropoietin, colony stimulating factors, e.g., GM-CSF, G-CSF, or M-CSF, interleukins, e.g., IL-1, -2, -3, -4, -5, -6, -7, -8, etc., or the like, or stromal cells associated with the stem cells becoming committed to a particular lineage, or with their proliferation, maturation and differentiation. The CDw109$^+$ cells may also be used in the isolation and evaluation of factors associated with the differentiation and maturation of hematopoietic cells. Thus, the CDw109$^+$ cells may be used in assays to determine the activity of media, such as conditioned media, evaluate fluids for cell growth activity, involvement with dedication of particular lineages, or the like.

The CDw109$^+$ cells may be used in gene therapy for the treatment of a variety of diseases, particularly genetic diseases. Genetic diseases associated with hematopoietic cells may be treated by genetic modification of autologous or allogeneic stem cells to correct the genetic defect. For example, diseases including, but not limited to, β-thalassemia, sickle cell anemia, adenosine deaminase deficiency, recombinase deficiency, recombinase regulatory gene deficiency, etc. may be corrected by introduction of a wild-type gene into the CDw109$^+$ cells, either by homologous or random recombination. Other indications of gene therapy are introduction of drug resistance genes to enable normal stem cells to have an advantage and be subject to selective pressure during chemotherapy. Suitable drug resistance genes include, but are not limited to, the gene encoding the multidrug resistance (MDR) protein.

Diseases other than those associated with hematopoietic cells may also be treated by genetic modification, where the disease is related to the lack of a particular secreted product including, but not limited to, hormones, enzymes, interferons, growth factors, or the like. By employing an appropriate regulatory initiation region, inducible production of the deficient protein may be achieved, so that production of the protein will parallel natural production, even though production will be in a different cell type from the cell type that normally produces such protein. It is also possible to insert a ribozyme, antisense or other message to inhibit particular gene products or susceptibility to diseases, particularly hematolymphotropic diseases.

Alternatively, one may wish to remove a particular variable region of a T-cell receptor from the T-cell repertoire. By employing homologous recombination, or antisense or ribozyme sequence which prevents expression, the expression of the particular T-cell receptor may be inhibited. For hematotrophic pathogens, such as HIV, HTLV-I and II, etc. the stem cells could be genetically modified to introduce an antisense sequence or ribozyme which would prevents the proliferation of the pathogen in the stem cell or cells differentiated from the stem cells. Methods for recombination in mammalian cells may be found in Molecular Cloning, A Laboratory Manual (1989) Sambrook, Fritsch and Maniatis, Cold Spring Harbor, N.Y.

The present invention further encompasses methods for obtaining compositions of cells which are highly enriched in stem cells. The method comprises incubating the compositions described above under conditions suitable for regeneration of stem cells. Compositions comprising the original stem cells and/or the regenerated stem cells are obtained thereby.

In another embodiment of the invention, a composition highly enriched in stem cells is provided. Such a composition has utility in reconstituting human hematopoietic systems and in studying various parameters of hematopoietic cells as described above.

The following examples are meant to illustrate but not limit the invention.

EXAMPLE 1

Purification of CD34$^+$CDw109$^+$ cells from fetal bone marrow (FBM)

Human fetal bones were dissected from 18–24 week old fetuses obtained by elective abortion with informed consent. Bone marrow (BM) cell suspensions were prepared by flushing split long bones with Iscove's modified Dulbecco's medium (IMDM, JRH Biosciences, Lenexa, Kans.) containing 5% heat-inactivated fetal calf serum (FCS, Hyclone Laboratories, Logan, Utah). Erythrocytes were lysed by 5 minutes (min) incubation with 0.83% ammonium chloride solution.

Glycoprotease positive selection of $CD34^+$ cells $CD34^+$ cells were selected according to the method described by Marsh et al. (1992) *Leukemia* 6:926–934. In brief, BM cells were resuspended in staining buffer (SB): Hanks buffered saline solution (JRH Biosciences) containing 10 mM Hepes (Sigma, St. Louis, Mo.) and 2% heat-inactivated FCS (Hyclone) or 0.5% BSA at $5 \times 10^7$ cells/mi. QBEND10 (anti-CD34, Amac, Westbrook Me.) was added at $\frac{1}{100}$ dilution, and the cells were incubated on ice for 30 min. The cells were then washed in SB with a FCS underlay, and resuspended at $4 \times 10^7$/ml in SB. An equal volume of washed Dynal sheep anti-mouse $IgG_1Fc$ magnetic beads (Dynal, Oslo, Norway), was added at a 1:1 bead to cell ratio, to give a final cell concentration of $2 \times 10^7$ cells/ml. After 30 min incubation on ice, with gentle inversion, the tube was placed against a Dynal magnet (Dynal) for 2 minutes, and $CD34^-$ cells were removed. Followed two washes, 20 µl of 'glycoprotease' (O-sialoglycoprotein endopeptidase, Accurate Chemical, Westbury, N.Y.) plus 180 µl of RPMI (JRH Biosciences)/20% FCS were added and the beads incubated at 37° C. for 30 min to cleave the QBEND10 epitope, and release $CD34^+$ cells from the beads. Beads were then washed three times to maximize cell recovery.

Isolation of $CDw109^+$ and $CDw109^-$ subpopulations from CD34-selected FBM cells by FACS Selected cells were then stained with a MAb to CD34 (T ük3, obtained from Dr. A. Ziegler, University of Berlin) plus anti-CDw109, 8A3-biotin at $\frac{1}{50}$ or with an $IgG_{2a}$-biotin control (Caltag, San Francisco, Calif.). After washing, cells were incubated with streptavidin-phycoerythrin (SA-PE) (Caltag, So. San Francisco, Calif.) to detect CDw109 and with Texas Red-conjugated goat anti-mouse IgG3 antibody (Southern Biotechnologies Associates, Birmingham, Ala.) to detect CD34. After a final wash, cells were resuspended in propidium iodide (1 µg/ml, Sigma) and sorted on the FACStar Plus Cell Sorter (Becton Dickinson, San Jose, Calif.) equipped with dual argon lasers. $CD34^+CDw109^+$ and $CDw109^-$ subpopulations were sorted using a lymphoblastoid gate and excluding cells with high propidium iodide uptake. Reanalysis of the sorted populations using the original sort gates gave an estimate of their purity.

EXAMPLE 2

Expression of CDw109 in hematopoietic cells

In order to determine the expression of CDw109 on different hematopoietic cell types the following experiments were performed.

Fetal bone marrow (FBM)

FBM cells were obtained and sorted by the glycoprotease method, as described in Example 1, into $CD34^-$ and $CD34^+$ cells. These cells were then analyzed by FACS to determine the concomitant expression of CDw109. It was found that CDw109 was expressed almost exclusively on $CD34^+$ cells, with less than 1% of $CD34^-$ cells positive for CDw109.

TABLE 3

| FBM | week gestation | % of $CD34^+$ positive for CDw109 |
| --- | --- | --- |
| S069 | 18 | 11.2 |
| L591 | 20 | 28.5 |
| S076 | 24 | 1.3 |
| SF275 | 19.5 | 16.9 |
| OA107 | 24 | 14.3 |
| mean |  | 14.4 |

A typical sort profile is shown in FIG. 1. It has proved difficult to purify the $CD34^+CDw109^+$ subset to greater than 70% purity, possibly due to photobleaching or loss of the molecule from the cell surface (it is linked to a glycophosphatidylinositol membrane anchor).

Figure 2A:
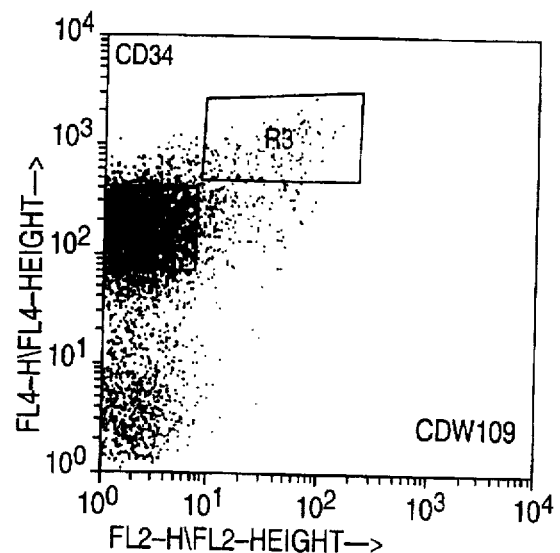
FIGS. 2A–2C show FACS analyses of CD38 expression on CDw109 subpopulations of FBM CD34$^{hi}$ cells.
Figure 2B:
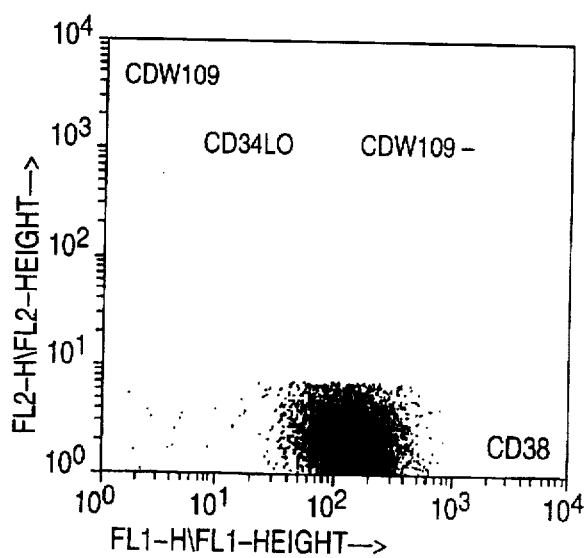
Figure 2C:
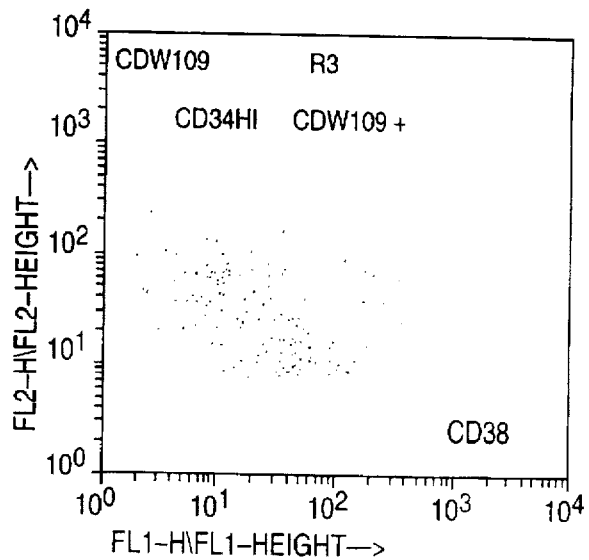
Figure 3A:
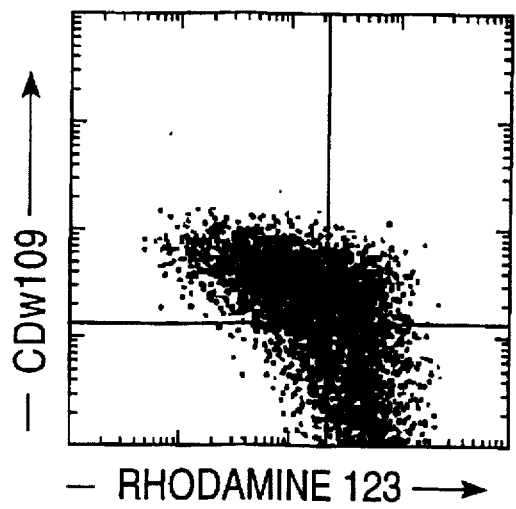
FIGS. 3A–3D show FACS analyses depicting rh1231$^{lo}$ primitive hematopoietic CD34$^+$ ABM cells expressing both CDw109 and Thy-1.
Figure 3B:
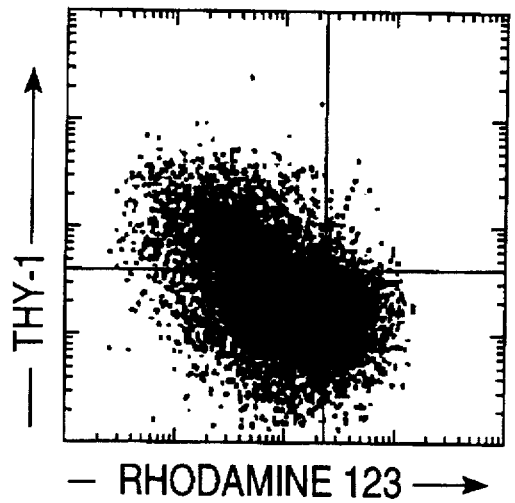
Figure 3C:
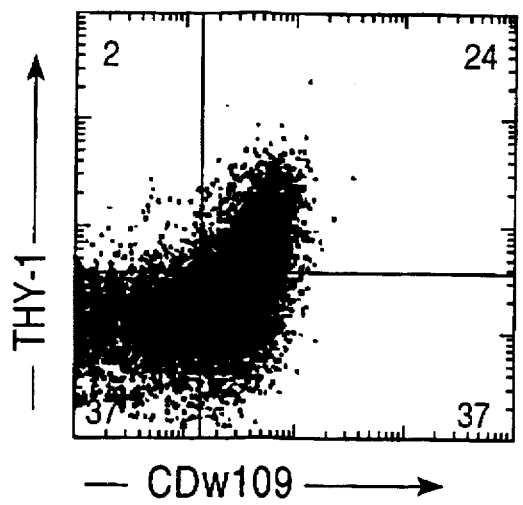
Figure 3D:
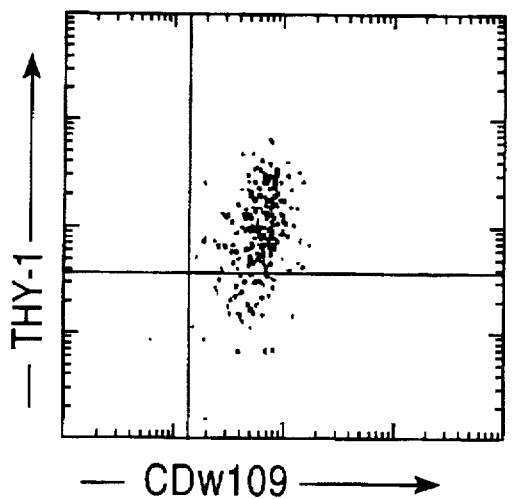
Figure 4A:
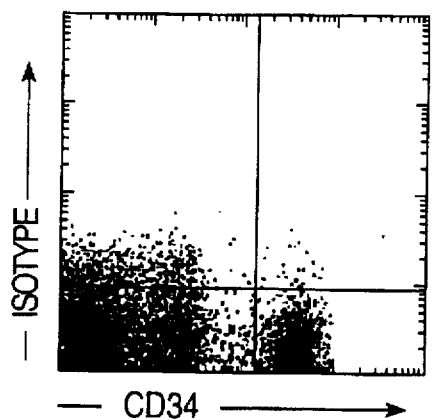
FIGS. 4A–4F show FACS analyses depicting rh123$^{lo}$ primitive hematopoietic CD34$^+$ MPB cells expressing both CDw109 and Thy-1.
Figure 4B:
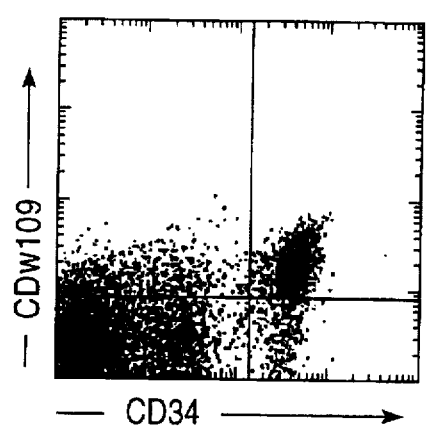
Figure 4C:
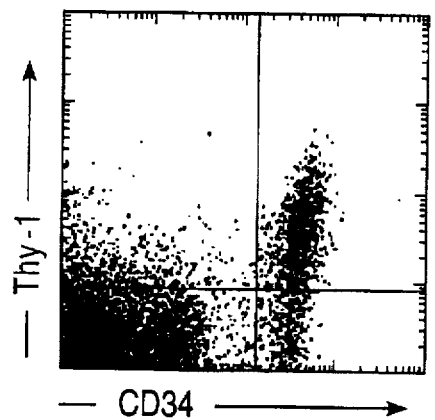
Figure 4D:
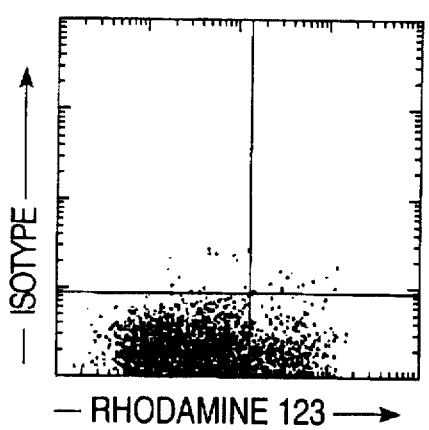
Figure 4E:
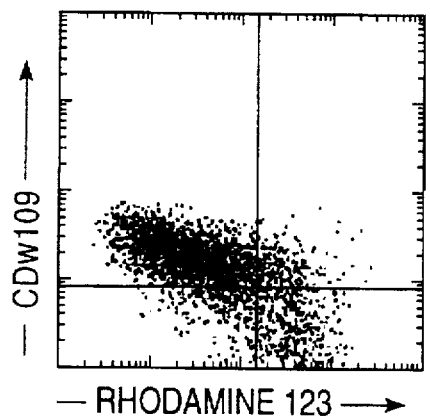
Figure 4F:
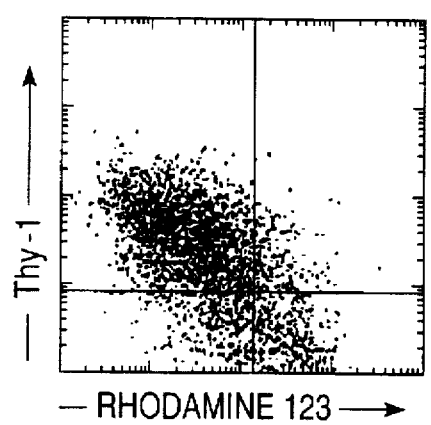
Figure 6A:
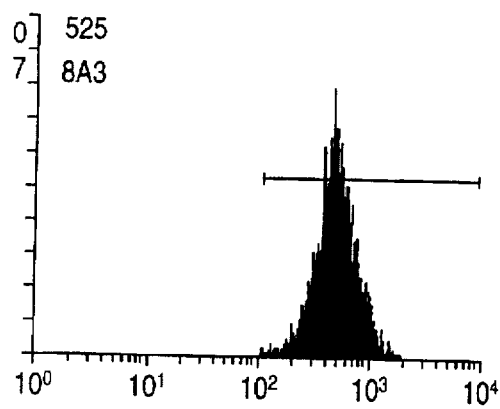
FIGS. 6A–6F depict additive results of additive binding studies using the αCDw109 antibodies 8A3, 7D1, 8A1, 40B8 and 7C5.
Figure 6B:
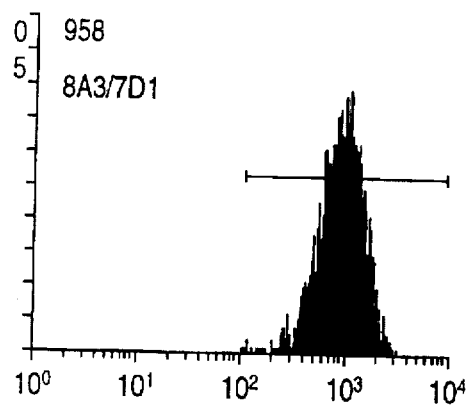
Figure 6C:
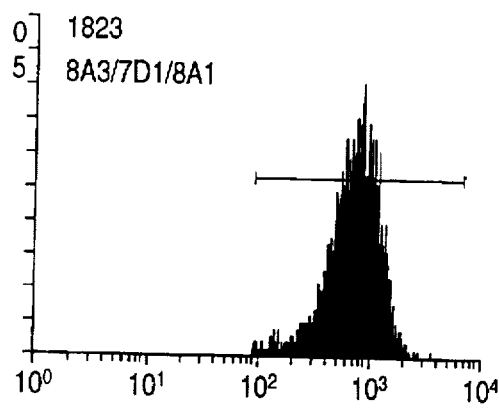
Figure 6D:
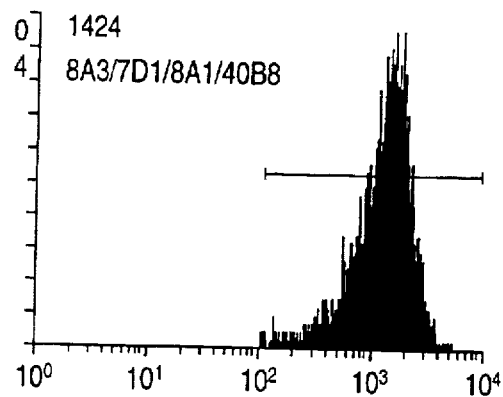
Figure 6E:
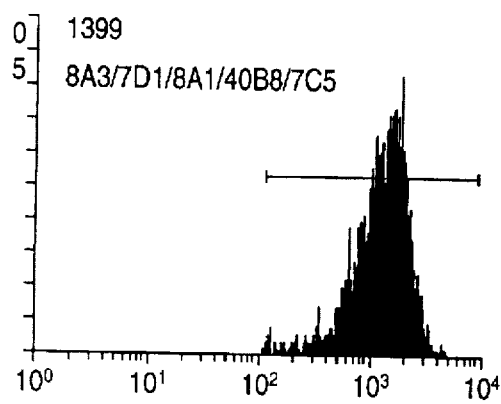
Figure 6F:
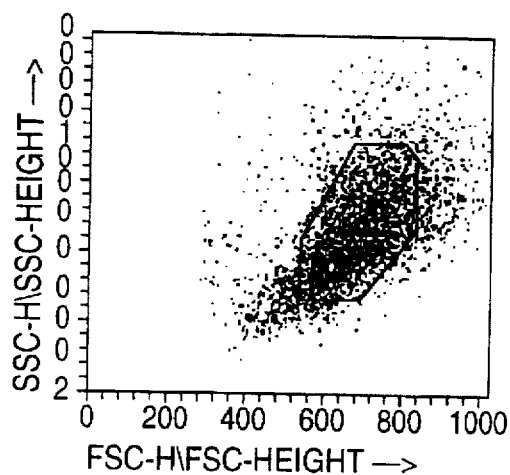
Figure 7A:
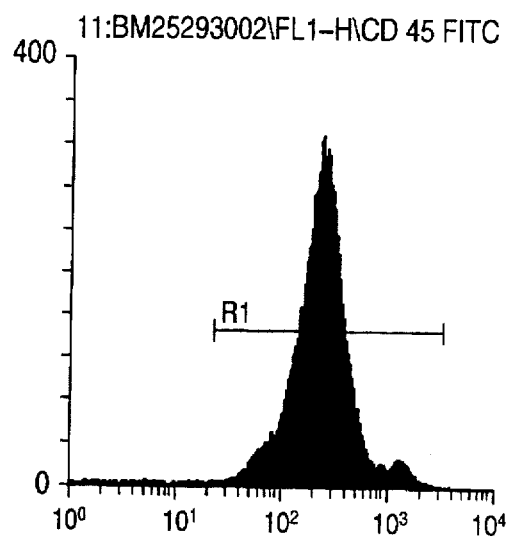
FIGS. 7A–7N show FACS analyses of (FIGS. 7A–7G) three-color analysis of ABM MNC stained with CD34, CD45 and CDw109 antibodies.
Figure 7B:
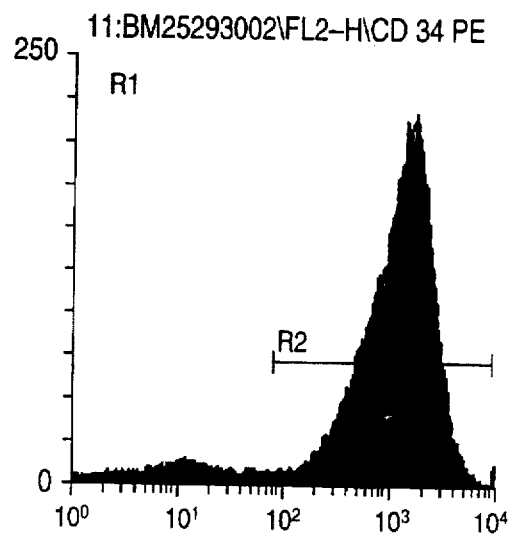
Figure 7C:
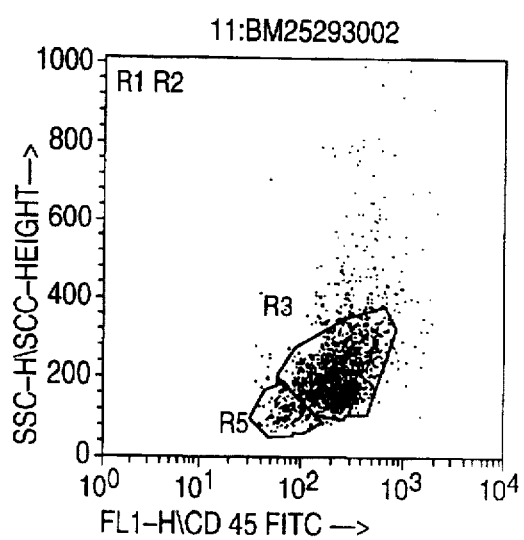
FIG. 7C depicts three antibody staining in both R1 R2 selected cells.
Figure 7D:
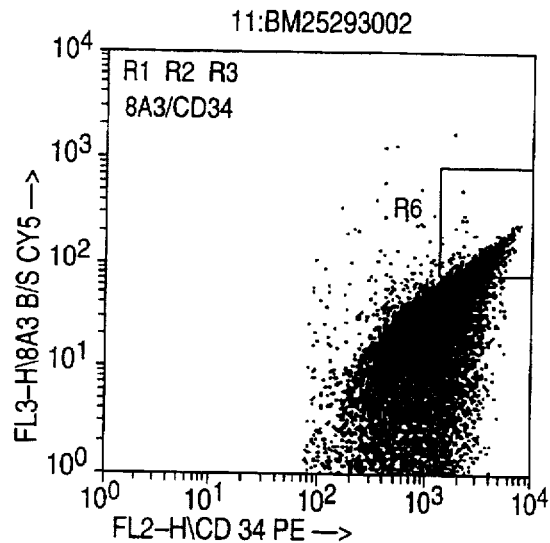
FIGS. 7D–7F depict, three color staining of R1, R2, R3 cells; R1, R2, R5 cells and R1, R2, R3, R5 cells.
Figure 7E:
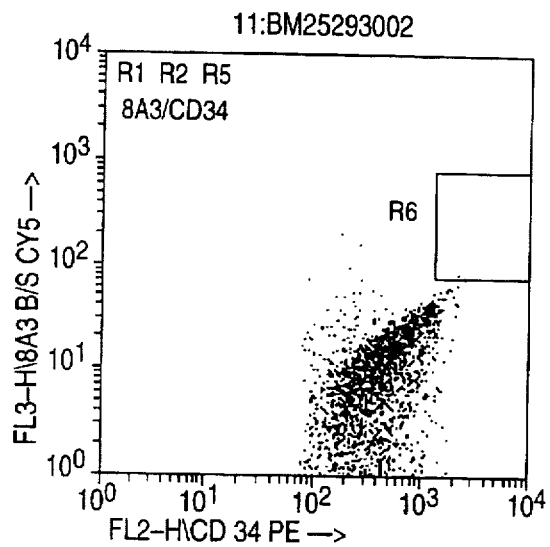
Figure 7F:
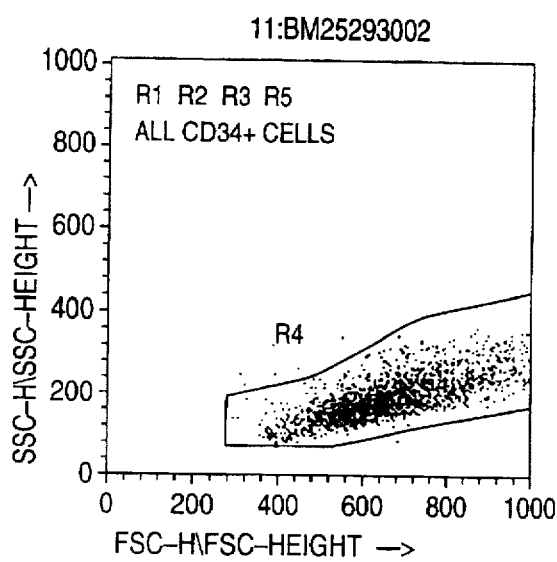
Figure 7G:
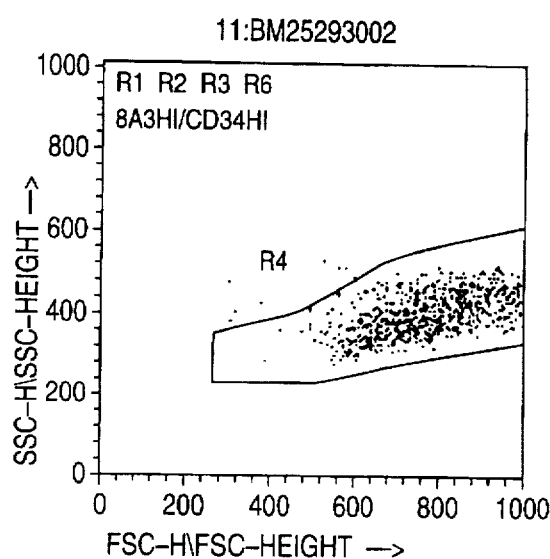
FIG. 7G shows staining in R1, R2, R3 and R6 cells and (FIGS. 7H–7N) three-color analysis of ABM MNC stained with CD34, CD45 and Thy-1 antibodies
Figure 7H:
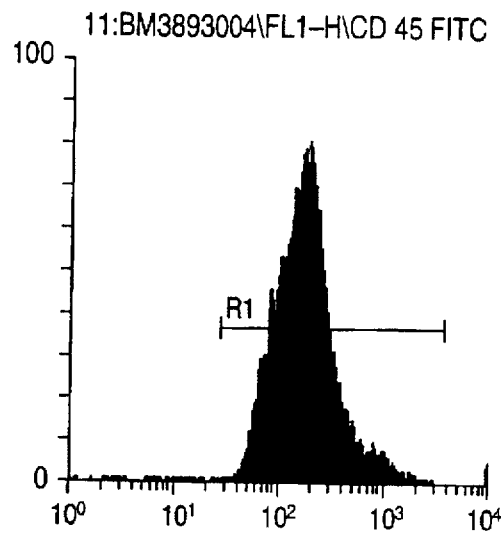
FIGS.7H and 7I depict two groups (R1 and R2) of ABM MNC cells selected for staining.
Figure 7I:
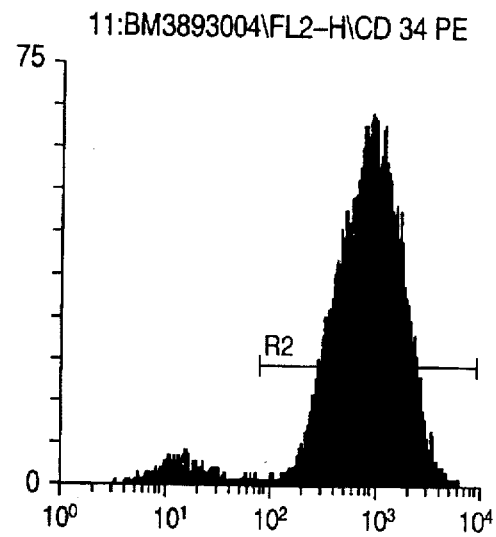
Figure 7J:
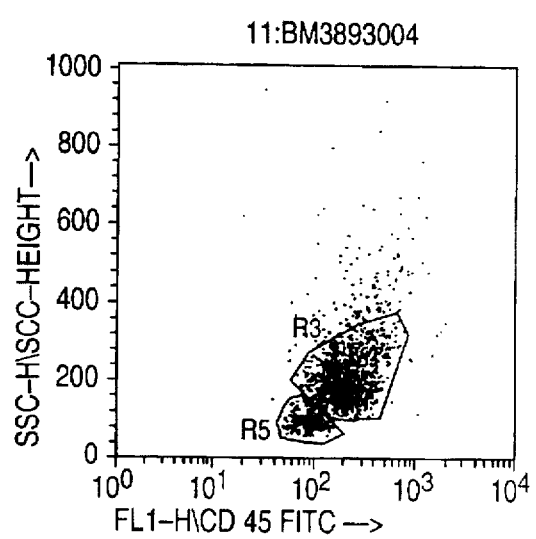
FIG. 7J depicts three antibody staining in both R1 and R2 selected
Figure 7K:
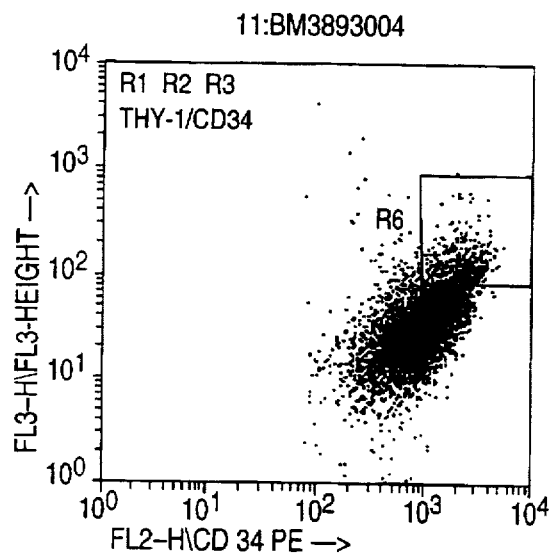
FIGS. 7K–7M depict three color staining of R1, R2, R3 cells; R1, R2, R5 cells and R1, R2, R3, R5 cells.
Figure 7L:
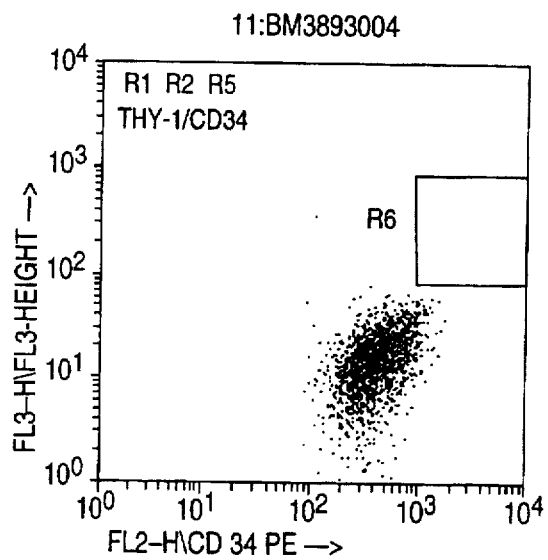
Figure 7M:
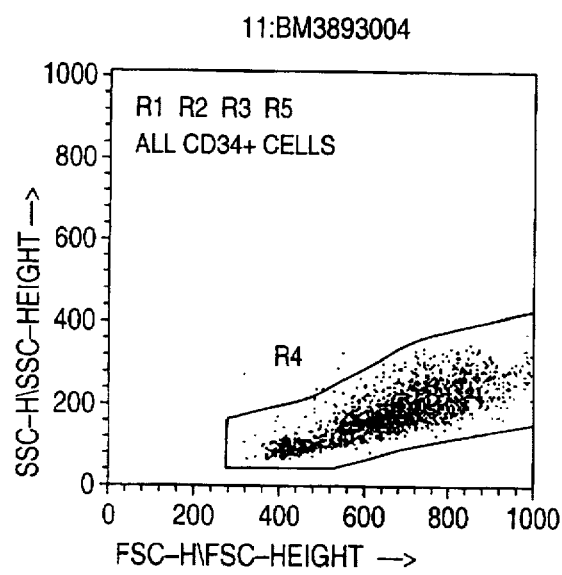
Figure 7N:
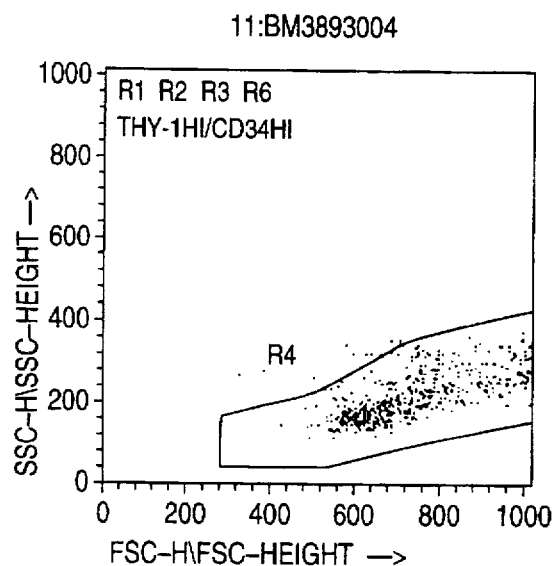

$CD34^{hi}$ cells obtained from FBM as described by DiGiusto et al. (1994) and stained for CD38 and CDw109. The results obtained are depicted in FIG. 2 (showing only the lymphoblastoid gate) and indicate that the $CD34^{hi}CDw109^+$ (FIG. 2A) population includes both $CD38^-$ and $CD38^+$ cells (FIG. 2C), while almost all $CD341^{lo}CDw109^-$ cells express high levels of CD38 (FIG. 2B).

Expression of CDw109 on adult hematopoietic cells a) Adult Bone Marrow (ABM)

The ABM cells were obtained, sorted and stained as described in Example 1. The ABM was obtained from normal BM aspirates, separated by ficoll density gradient, and a $CD34^+$ selection done on a CellPro column according to the manufacturer's instructions. The Thy-1 antibody was GM201, which was detected using a goat anti-mouse IgG1-Texas Red conjugate from Southern Biotechnology Associates. The CDw109 antibody was 8A3, detected with goat anti-mouse IgG2a-PE conjugate from Caltag.

The results obtained are depicted in FIGS. 3A through 3D. About 10% of $CD34^+$ cells express CDw109. The results shown in FIGS. 3A through 3D show that $CD34^+CDw109^+$ cells include all of the $rho^{lo}$ subset, which is known to contain stem cells. The $CDw109^+$ population was also found to include some $rho^{mid}$ and both $Thy-1^+$ and $Thy-1^-$ staining cells. Thus, the $CDw109^+$ population contains stem cells and some progenitor cells.

b) Mobilized peripheral blood (MPB)

Apheresed samples were obtained with informed consent from multiple myeloma patients treated at the University of Arkansas Medical Center. The patients were treated on day 1 with cyclophosphamide at 6 g/m² (1.5 g/m² every 3 hrs×4 doses). From day 1 until the start of leukopheresis (usually 10–28 days), granulocyte macrophage colony stimulating factor (GM-CSF) was given at 0.25 mg/m²/day. Apheresis for total white cells was started when the peripheral blood white cell count was greater than 500 cells/µl and the platelet count was greater than 50,000 cells/µl. Patients were apheresed daily until from $6 \times 10^8$ mononuclear cells (MNC) were collected. The leukopheresis sample was subject to ammonium chloride lysis to remove RBCs, then stained with rhodamine, then with CD34 and either Thy-1 or CDw109 as described above for ABM except that both the Thy-1 and CDw109 were detected with PE conjugates of the appropriate goat anti-mouse IgG from Caltag.

The results obtained are depicted in FIGS. 4A through 4F. In one analysis, 78.5% of $CD34^+$ cells mobilized into peripheral blood expressed a low level of CDw109. This higher expression on MPB $CD34^+$ cells is similar to Thy-1. As in ABM, CDw109 expression is similar to Thy-1 including expression on the $rho^{lo}$ subset, which contains stem cells.

EXAMPLE 3

Colony formation assays of CDw109+ cells

The FBM cells sorted for CD34+CDw109+ cells as described in Example 2 were placed in assays for colony forming cells and in the CAFC assay for stem cells (Example 4). Their potential to give rise to megakaryocytes (MKs) was determined using both the fibrin clot MK colony assay and short term culture in 10% aplastic anemia serum (AAS, Indiana University), which drives the differentiation of MKs. For the CAFC experiments, the ABM was obtained from a normal BM aspirate, then separated by ficoll density gradient, and the CD34+ selection done using the glycoprotease method described in Example 1.

Methylcellulose Colony Assay

FBM CD34+CDw109+ and CD34+CDw109− cells were plated at a concentration of 5×10³ cells per ml of Iscove's methylcellulose (Terry Fox Laboratory) according to the method described by Brandt et al. (1992) *Blood* 79:634–641, in the presence of IL-3 (10 ng/ml), GM-CSF (2 ng/ml), steel factor (100 ng/ml) and erythropoietin (2 units/ml) (Amgen Inc., Thousand Oaks, Calif.). Colonies were scored after 14 days of incubation in 5% $CO_2$ at 37° C. in a humidified atmosphere. The results obtained are presented in Table 5. In day 14 methylcellulose assays, the CD34+CDw109+ subset contained all the BFU-E and CFU-mix, as well as 90% of the CFU-GM colonies.

enriched in the CDw109+ subset of FBM CD34+ cells. The results obtained indicate that CD34+CDw109+ are enriched for CFU-mix, CFU-GM, BFU-E, BFU-MK and CFU-MK, i.e., all progenitors of the myeloid/mega/erythroid lineages.

Eleven day suspension culture in 10% aplastic anemia serum

Cells were counted and 2.5–7×10⁴ cells plated in wells of flat-bottom 96 well plates (Corning) in medium containing IMDM/α-thioglycerol and 10% aplastic anemia serum (Indiana University Medical School). Every 3–4 days, cells were transferred to new wells to remove adherent cells, and fed with fresh medium so as not to exceed 5×10⁴ cells/100 μl At days 4, 7 and 11, cells were harvested, counted and, when sufficient cells were present, cytospins prepared and stained with Wright-Giemsa, or acetone fixed (5 min) for immunocytochemical staining. MAbs used to stain the cells included 8D9 (anti-gpIIb (CD41), SyStemix Inc.), anti-thrombospondin (Amac, Westbrook, Me.) and CD68 (Dako Corp., Carpinteria, Calif.). Primary antibodies were detected using biotinylated horse anti-mouse IgG (1/100) (Vector Labs, Burlingame, Calif.). After final incubation with streptavidin-alkaline phosphatase (1/200) (Caltag), slides were washed and the substrate was added (naphthol AS-MX phosphate (Sigma, St. Louis, Mo.)), fast red TR salt (Sigma) in propandiole buffer pH 9.75, containing levamisole HCl (Sigma) and incubated for 20 min. Final washes were in tap water, and slides were counterstained for 10 seconds in hematoxylin (Gill no. 3 Sigma), washed, dried and mounted

TABLE 5

CD34+CDw109+ cells from FBM contain CFU-GM, BFU-E, CFU-mix and the MK progenitors BFU-MK and CFU-MK

| FBM | Population | CFU-GM | BFU-E | CFU-mix | BFU-MK | CFU-MK |
|---|---|---|---|---|---|---|
| S069 | CD34+CDw109+ | 2960 +/− 0 | 320 +/− 113 | 120 +/− 57 | 7 +/− 1.4 | 54 +/− 8.4 |
|  | CD34+CDw109− | 267 +/− 92 | 0 +/− 0 | 0 +/− 0 | 1 +/− 1.4 | 0 +/− 0 |
| L591 | CD34+CDw109+ | 1627 +/− 122 | 960 +/− 288 | 565 +/− 72 | 7 +/− 0.7 | 17 +/− 0.7 |
|  | CD34+CDw109− | 107 +/− 46 | 0 +/− 0 | 0 +/− 0 | 0 +/− 0 | 2 +/− 0.7 |
| S076 | CD34+CDw109+ | 2400 +/− 349 | 2533 +/− 533 | 1280 +/− 367 | 6 +/− 2.8 | ND |
|  | CD34+CDw109− | 347 +/− 122 | 133 +/− 122 | 0 +/− 0 | 1 +/− 1.4 | ND |

EXAMPLE 4

Megakaryocyte Potential

Fibrin Clot Assay

The fibrin clot assay was performed according to the method described by Bruno et al. (1988) *Exp. Hematol.* 16:371–377. Sorted FBM cells were plated at 5×10³/ml in the presence of IL-3 at 10 ng/ml (Sandoz, Basel, Switzerland), GM-CSF at 2 ng/ml (Sandoz) and steel factor at 100 ng/ml (R & D Systems, Minneapolis, Minn.). The optimal concentrations of cytokines have been previously reported by Bruno et al (1988); Bruno et al. *Blood* 73:671 (1989); and Bridell et al. (1989) *Blood* 74:145. The cells were incubated for 12 days and the CFU-MK were measured. The cells were fixed in methanol/acetone (1:3) and washed first in PBS, then $dH_2O$. The cells were stained with antibody 8D9 specific for gpIIb and then goat anti-mouse IgG-FITC (Kirkegard and Perry) and Evans Blue counterstain. Positive colonies are fluorescent green and negative colonies are dull red. Where the colonies are all pure CFU-MK, all the cells in the colony express gpIIb; where they are mixed CFU-MK, a proportion of the cells in the colony are gpIIb+ (usually at the periphery). The BFU-MK assay is the same assay read at day 21, scoring multifocal colonies.

Figure 8:
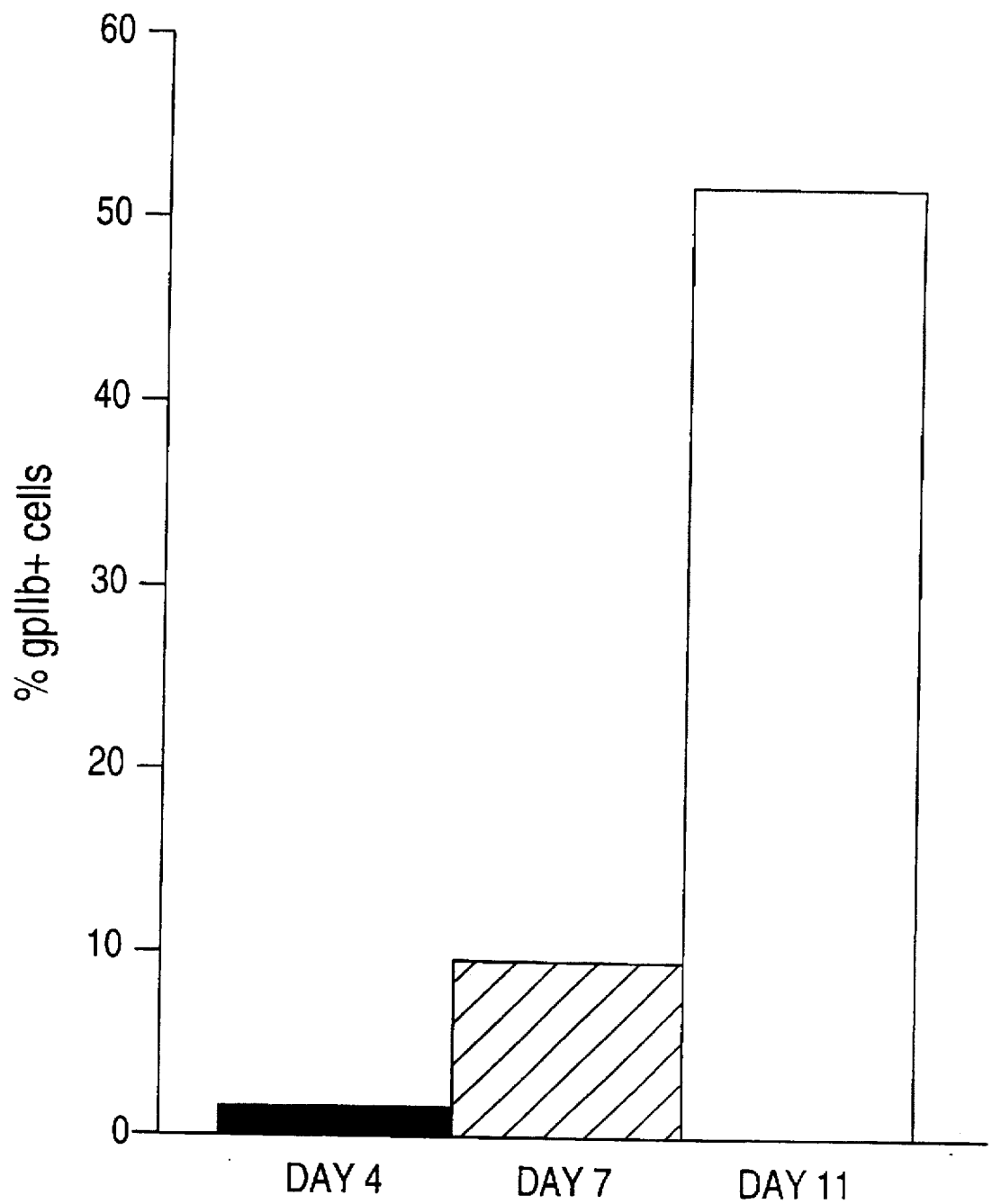
FIG. 8 is a bar graph depicting the increase in percentage of MKs generated from CD34$^+$CDw109$^+$ cells in 10% AAS.

The results of the colony assays are summarized in Table 5 and show that BFU-MK and CFU-MK activity is highly using crystal/mount (Biomeda Corp., Foster City, Calif.). The results are shown in Table 6 and FIG. 8.

Analysis of MK Potential

In previous liquid culture experiments to drive MK maturation, more than 10% CD41+ cells had never been observed at 10–11 days. The CD34+CDw109+ population, cultured for 11 days in 10% AAS gave rise to 52% CD41+ cells, together with a large population of macrophages. Averaging three experiments, 35% CD41+ cells (FIG. 8) were observed a day 11. The presence of IIb+ MKs (24.6%) was confirmed by a similar % staining with anti-thrombospondin (25.8%), and the recognition of 22% MKs by morphology (Wright-Giemsa staining). This CD34+ CDw109+ subpopulation of FBM clearly contains MK progenitors, which give rise to some large polyploid MKs under stimulation by AAS. The results are shown in Table 6. In Table 6, Expn. means fold expansion in total cell number since the previous plating; immunostaining was performed using the alkaline phosphatase technique; IIb and TSP (thrombospondin) are MK markers; CD68 stains macrophages; and in two out of three experiments, the CDw109+ subset of CD34+ cells showed a low level of expansion in AAS.

TABLE 6

| | | Short Term Culture in Aplastic Anemia Serum | | | | | |
|---|---|---|---|---|---|---|---|
| FBM | Population | d0 cell no. | d7 expn | d11 expn | d11% gpIIb+ | d11% TSP+ | d11% CD68+ |
| 1 | 34+109+ | 2.5 | 1.6 | 2 | 24.6 | 25.8 | 30 |
|   | 34+109− | 2.5 | ND | ND | ND | ND | ND |
| 2 | 34+109+ | 5.5 | 0.73 | 1.2 | 35 | 17.6 | 36.1 |
|   | 34+109− | 5.5 | 0.84 | 1.09 | 6.6 | 7.7 | 73.7 |
| 3 | 34+109+ | 7.0 | 1.7 | 1.8 | 16 | 15.5 | 79.5 |
|   | 34+109− | 7.0 | 0.57 | 0 | 0 | ND | ND |

Stimulation of MK Development Using Mpl Ligand

In order to determine the effect of Mpl ligand on CDw109+ cells, FBM (19 wk) 2–4% of CD34+ were CDw109+ plated cells in 10% Mpl ligand containing COS supernatant and 5% human plasma. Mpl ligand cDNA was cloned using the polymerase chain reaction from human fetal liver cDNA (Clontech, Palo Alto, Calif.), using oligonucleotides based on the published sequence, and expressed in COS cells. Mpl ligand-containing supernatants were shown to be active in stimulating the proliferation of Mpl receptor-expressing BAF-3 cells (>5×10$^5$ U/ml, where 50 U=50% maximum activity), which were constructed by stable transfection of BAF-3 cells with a human Mpl receptor expression construct, essentially as described by de Sauvage et al. (1994) Nature 369:533; Kaushansky et al. (1994) Nature 369:568; Wendling et al. (1994) Nature 369:571; and Bartley et al. (1994) Cell 77:1.

5×10$^4$ cells of each sorted cell subpopulation were placed in individual wells of a 96 well plate in 100 μl of IMDM/5% normal human plasma and 10% COS supernatant containing human Mpl ligand. The number of total cells was counted at days 4, 7 and 11, and cytospins were prepared when sufficient cells were present. At these time points, cells were transferred to new wells, and fed with fresh medium so as not to exceed 5×10$^4$ cells/100 μl. Cytospins were stained as to enumerate the percentage of gpIIb+ cells. The results obtained are presented in Tables 7 and 8.

TABLE 7

| | Total Cell Count (x 10$^4$) | | | |
|---|---|---|---|---|
| | Day 0 | Day 4 | Day 7 | Day 11 |
| CD34+CDw109+ | 4.7 | 8.6 | 9.3 | 6.8 |
| CD34+CDw109− | 10 | 7.9 | 3.6 | 1.3 |

TABLE 8

| | % of gpIIb+ MKs | | |
|---|---|---|---|
| | Day 4 | Day 7 | Day 11 |
| CD34+CDw109+ | 68.4 | 71 | 85.7 |
| CD34+CDw109− | <1 | <1 | 3.4 |

EXAMPLE 5

In vitro co-culture of CDw109+ cells on AC6.21 cells for myeloid and B-cell differentiation The results obtained in Example 3 indicate that the CD34+CDw109+ population is enriched for all colony forming cells in FBM, including the relatively primitive progenitors, BFU-MK and CFU-mix. The fact that 8A3 has now been found to stain the majority of CD34$^{hi}$ cells, which have previously been shown to contain the fetal stem cells, led to the hypothesis that CDw109 is expressed by hematopoietic stem cells. In order to demonstrate this, CDw109± subsets of CD34+ cells were placed in limiting dilution onto AC6.21 cells in the presence of LIF and IL-6.

AC6.21 mouse BM stromal cells were plated in Whitlock-Witte media in wells of polystyrene flat-bottom 96 well plates (Corning, Corning, N.Y.), and allowed to form a confluent adherent layer. After 1–2 weeks, sorted cells were plated on top of the confluent AC6.21 cells at limiting dilution (range usually 1000 to 30 cells/well, at least 24 wells per concentration) in long term culture medium (1:1 IMDM/RPMI, JRH BioSciences, Woodland, Calif.) containing 10% FCS (Hyclone Labs, Logan, Utah), 50 U/ml penicillin, 50 μg/ml streptomycin, 2 mM glutamine, 1 mM sodium pyruvate (JRH BioSciences) and 10$^{-6}$M 2-mercaptoethanol (Sigma, St. Louis, Mo.), in the absence of growth factors, or 100 to 1 cell/well in the presence of purified human recombinant interleukin-6 (IL-6, 10 ng/ml) and leukemia inhibitory factor (LIF, 50 ng/ml), provided by Sandoz Pharma Ltd. (Basel, Switzerland). Cultures were fed weekly with medium containing the same growth factors. In the presence of growth factors, cobblestone areas of more than 50 cells were usually counted from 2–5 weeks. At 5 weeks, cells were harvested and stained with CD33-PE and CD19-FITC or CD34 (HPCA2)-PE (Becton Dickinson) or relevant isotype controls, and analyzed on a FACScan. The frequency of CAFC was calculated by the cell number at which 37% of the wells show no growth of cobblestone areas, using regression, with 95% statistical precision according to the method described by Lefkovits and Waldmann (1984) Immunol. Today 5:265.

The frequencies of CAFC in FBM were determined between 2 and 5 weeks, and are summarized in Table 9(a). Table 9(b) shows the number of wells containing more than 1% cells positive for CD33 (myeloid cells), CD19 (B cells) or CD34 (progenitors) over the number of wells analyzed and the ranges of positively staining cells. The ABM CAFC frequencies at weeks 4 and 5 are shown in Table 9(c).

TABLE 9

| a) CAFC frequency | | | | | |
|---|---|---|---|---|---|
| FBM | Population | week 2 | week 3 | week 4 | week 5 |
| L591 | CD34+CDw109+ | 1/374 | 1/411 | 1/258 | 1/114 |
|   | CD34+CDw109− | <1/10,000 | <1/10,000 | <1/10,000 | <1/10,000 |
| S076 | CD34+CDw109+ | 1/43 | 1/28 | 1/26 | 1/31 |
|   | CD34+CDw109− | <1/10,000 | <1/10,000 | <1/10,000 | <1/10,000 |
| SF275 | CD34+CDw109+ | 1/290 | 1/292 | 1/339 | 1/352 |
|   | CD34+CDw109− | <1/10,000 | <1/10,000 | <1/10,000 | <1/10,000 |
| OA107 | CD34+CDw109+ | 1/68 | 1/45 | 1/71 | 1/95 |
|   | CD34+CDw109− | <1/10,000 | <1/10,000 | <1/10,000 | <1/10,000 |

| b) Analysis of CAFC positive wells from CD34+CDw109+ cells for B, myeloid and CD34+ cells | | | |
|---|---|---|---|
| FBM | CD33+ | CD19+ | CD34+ |
| L591 | 4/5 | 3/5 | 2/5 |
| range | 1.4–91% | 27.2–56.9% | 4.3–14.8% |
| S076 | 19/20 | 15/20 | 16/20 |
| range | 3–85% | 2.5–52.8% | 1.1–15% |
| SF275 | 7/7 | 4/7 | 6/7 |
| range | 24.9–96.8% | 1.02–47.9% | 1.1–54.5% |
| OA107 | 14/19 | 15/19 | 4/19 |
| range | 1.1–61.2% | 34–86.2% | 1.1–13.5% |

TABLE 9-continued

(c) Adult Bone Marrow CKFC Frequency

| Population | Week 4 | Week 5 |
| --- | --- | --- |
| CD34⁺CDw109⁺ | 1/17 | 1/15 |
| CD34⁺CDw109⁻ | 1/51 | 1/51 |

These results indicate that cells forming cobblestone areas in 5 week coculture with a murine stromal cell line AC6.21 were exclusively contained within the CDw109⁺ subset of CD34⁺ cells from FBM. Phenotypic analysis demonstrated a high level of CD34⁺ cell maintenance, B cell and myeloid cell co-production after 5 weeks in culture indicating the presence of HSC activity in this CDw109⁺ subset. CAFC frequency was enriched in the CDw109⁺ subset of CD34⁺ cells from ABM compared to the CDw109⁻ subset. The difference is not as striking as that seen in FBM, which may be due to sort purity.

EXAMPLE 6

(a) Lymphoid Potential

It is possible that the CD34⁺CDw109⁻ population, which fails to score in either the colony or stem cell in vitro assays, represent lymphoid progenitors. The scatter profile of this population resembles small, possibly lymphoid cells.

CD34⁺CDW109⁻ FBM cells obtained as described in Example 1 were stained with anti-IgG1-PE, CD2-PE, CD19-PE, CD20-PE, CD23-PE, and analyzed on FACSCAN. The results obtained are presented in Table 10.

TABLE 10

| |
| --- |
| 2.5% CD2⁺ (T + NK cells) |
| 97.9% CD19⁺ (marks all B cells) |
| 55.4% CD20⁺ (later B cell marker) |
| 0.2% CD23⁺ (only mature B cells) |

The results show that the CD34⁺CDw109⁻ cells are virtually all lymphoid progenitor cells. In addition, CD34⁺ CDw109⁺ cells are substantially negative for the lymphoid markers CD10 and CD19 (data not shown ). These results suggest that while the CD34⁺CDw109⁺ cells contain stem cells and megakaryocyte, myeloid and erythroid progenitors, they are depleted of lymphoid progenitor cells.

EXAMPLE 7

Identification of CDw109 subsets in unfractionated Adult Bone Marrow
Antibodies

Hybridoma 4B2 that produces an antibody ($IgG_{2a}$) which recognizes a 'framework' epitope on the CD45 antigen was obtained from the ATCC (accession no. HB 196). The hybridoma was grown in RPMI/10% FCS and secreted antibodies isolated from spent culture medium using Protein A-sepharose. Purified antibodies were conjugated to either fluorescein isothiocyanate (FITC), phycoerythrin (PE), cyto-chrome (Cy), or biotin using standard methods. Fluorochrome-conjugated antibodies HPCA2 or QBEnd10 to CD34 were obtained from Becton-Dickinson or Southern Biotechnology Associates respectively. PE conjugates of Thy-1 antibody 5E10 were obtained from Pharmingen. CDw109 antibodies 8A3 (IgG2), 7D1 (IgG1), 7C5 (IgG1) and 8A1 (IgG1) were isolated from spent tissue culture medium as described for 4B2 and purified either on Protein A-sepharose (8A3) or on Rabbit anti-Mouse Ig coupled to Protein A-sepharose according to the method described by Schneider et al. (1982) *J. Biol. Chem.* 257:10766–10769. CDw109 antibody 40B8 was obtained from Dr. Hans-Jorg Buhring. Biotinylated antibodies were visualized using streptavidin conjugated to cychrome (Southern Biotechnology Associates). Each antibody was titrated for maximal binding and subsequent experiments using CDw109 and Thy-1 antibodies were performed at appropriate concentrations to give maximal binding as determined by FACS.

Cells

The primitive myeloid/T-lymphoid cell line KG1a was obtained from the ATCC (accession no. CCL 246.1) and grown under standard conditions. A low density mononuclear cell (MNC) fraction of normal bone marrow was prepared using ficoll-hypaque (Toronto Hospital).

Staining and analysis of cells

For epitope mapping studies, quintuplicate aliquots of KG1a cells (0.5–1×10⁶/analysis) were incubated for 30 min on ice with either 5 μl 8A3, 7D1, 7C5 or 8A1. 2 μl biotinylated conjugates of 8A3, 7D1, 7C5 or 8A1 were then added to each of the 4 sets of the above samples (i.e. 16 samples total for this experiment) for a further 30 min on ice. Cells were then washed twice in cold phosphate buffered saline by centrifugation and incubated with cychrome-conjugated streptavidin for a final 30 min on ice. Stained cells were then analyzed by flow cytometry using a FACS-can (Becton Dickinson Instrument Systems (BDIS)). The results obtained are presented in Table 11.

TABLE 11

Additive Binding of CDw109 Antibodies

| ANTIBODY 1-biotin (5 μl.) | ANTIBODY 2-biotin (2 μl.) | MEAN FLUORESCENCE |
| --- | --- | --- |
| 8A3 | 8A3 | 530 |
| 8A3 | 7D1 | 843 |
| 8A3 | 7C5 | 465 |
| 8A3 | 8A1 | 352 |
| 8A1 | 8A3 | 578 |
| 8A1 | 7D1 | 657 |
| 8A1 | 7C5 | 574 |
| 7D1 | 7D1 | 445 |
| 7D1 | 8A3 | 797 |
| 7D1 | 8A1 | 760 |
| 7D1 | 7C5 | 773 |
| 7C5 | 7C5 | 365 |
| 7C5 | 8A3 | 465 |
| 7C5 | 7D1 | 743 |
| 7C5 | 8A1 | 632 |

The results obtained indicate the following. The 7D1 epitope is probably unique. Antibodies 8A3 and 7C5 may identify the same epitope or epitopes that are close together, since 7C5 reduces the binding of 8A3 somewhat. Antibody 8A3 may therefore have a higher binding affinity than 7C5. Although antibody 8A1 is also a unique epitope, it is rather weak and may be close to the 8A3 epitope since a relatively small increase in binding is noted between 8A1 and 8A3 only, whereas a larger increase in binding is noted between 8A1 and 7D1. Antibody 8A3 gives the best individual binding and this is highly reproducible.

For additive binding studies, five aliquots of 5–10×10⁶ KG1a cells were incubated with 5 μl of biotinylated 'Antibody 1' at 4° C. for 30 minutes. 2μl of biotinylated 'Antibody 2' was then added for a further 30 minutes. The following combinations of antibodies were used: 8A3, 8A3+7D1, 8A3+7D1+8A1, 8A3+7D1+8A1 or 8A3+7D1+8A1+7C5. After two washes in ice-cold PBS containing 0.02%

NaN$_3$. 5 μl of cychrome-conjugated streptavidin was added. Analysis of samples was performed on a FACScan (Becton Dickinson Instrument Systems). Results from a representative experiment are shown in FIGS. 6A–6F. In cocktail experiments performed to date, the brightest fluorescence is found with 8A3, 7D1 and 40B8. 8A1 does not increase the binding much more over this cocktail.

For three color analysis involving CDw109 antibodies, BM MNCs were stained with a combination of CD45 FITC, CD34PE and CDw109 biotin/streptavidin cychrome. CD34$^+$ cells were identified by CD45 gating (to identify nucleated WBC), CD34 to identify CD34$^+$ WBCs, and the CD34$^+$ events back-gated to CD45 versus side scatter to identify true CD34$^+$ cells according to the method described by Sutherland et al. (1994) *Exp. Hematol.*22:1003–1010. CD34$^+$ cells were then analyzed for expression of CDw109, using either individual CDw109 antibodies, or a cocktail of CDw109 antibodies shown by the above experiments to identify non-overlapping epitopes on the CDw109 structure (8A3/7D1/40B8±8A1).

For three color analysis involving Thy-1 antibodies labeled with PE, true CD34$^+$ cells were gated/identified with CD45 biotin/streptavidin cychrome (or CD45 directly conjugated to cychrome) and CD34 FITC.

For three-color analysis of CD34$^+$ cells selected with glycoprotease as described in Example 1, adult BM MNCs were selected according to the method described by Marsh et al. (1992) *Leukemia* 6:926–934. Purity was assessed using CD34/CD45 according to the method described by Sutherland et al. (1994). CDw109 and/or Thy-1 antibodies were added as above. Results from representative experiments are shown in FIGS. 7A–7G (CDw109) and 7H–7N (Thy-1). The results show that the staining pattern for CDw109 on CD34$^+$ cells is similar to that for Thy-1, known to be expressed on stem cells, and the scatter profile resembles that expected for stem cells.

The initial experiments did not include antibody 40B8, however, subsequent analyses have confirmed that 40B8 recognizes an epitope different from those recognized by 8A3, 7D1 and 8A1.

EXAMPLE 8

In vivo stem cell assay.
SCID-hu bone assay

CB-17 scid/scid (SCID) mice bred in facilities at SyStemix, Inc., Palo Alto, Calif., are used between 6 to 8 weeks of age for the construction of SCID-hu bone mice according to the method described by Kyoizumi et al. (1992). Briefly, split fetal long bones are implanted subcutaneously into the mammary fat pads of SCID mice under anesthesia. HLA immunophenotyping of the recipient fetal bone and of donor ABM cells is performed with FITC-conjugated MA2.1, BB7.2, GAP-A3 and W6/32 MAbs derived from hybridomas obtained from the American Type Culture Collection (ATCC). SCID-hu bone mice are used 8 weeks post-implantation as recipients for HLA-mismatched sorted cell populations and are conditioned by receiving a single whole body irradiation dose (400 cGy from a $^{137}$Cs source, Gamma Cell 40, J. L. Shepherd & Associates). Sorted cells (3×10$^4$ in 10 μl) are then injected directly into the transplanted bone using a Hamilton syringe. After 8 weeks, mice are sacrificed and human bones removed. Flushed bone cells are resuspended into a red blood cell lysing solution, then washed twice in SB and counted before being stained for two-color immunofluorescence with FITC-labeled MAbs against the specific donor HLA allotype in combination with PE anti-CD19, -CD33, and -CD34. FITC and PE-conjugated irrelevant mouse immunoglobulins are used as negative controls. Cells are analyzed on a FACScan fluorescent cell analyzer (Becton Dickinson).

SCID-hu thymus assay.

HLA immunophenotyping of the recipient thymus and of donor ABM cells is performed as described above. Fragments of fetal thymus are placed on nitrocellulose filters (0.8 μm, Costar Corp., Cambridge, Mass.) on top of gelatin rafts (Gelfoam, Upjohn) according to the method described by Galy et al. (1993). After 7–13 days of incubation at 25° C. and 5% CO$_2$, thymus fragments are irradiated with 250 cGy from a $^{137}$Cs source (J. L. Shepherd & Associates), washed and immediately microinjected with the HLA-mismatched sorted cells in a 1 μl volume using an oil-filled microinjector (Narishige) and 1 mm diameter glass micropipettes (World Precision Instruments). Fragments are placed back on the filters and incubated at 37° C., 5% CO$_2$ overnight and then inserted under the kidney capsule of anesthetized 6–8 week old SCID mice. Mice are sacrificed 6 to 7 weeks after transplantation and the thymus grafts recovered, reduced to a single cell suspension, and subjected to three-color immunofluorescence analysis on the FACScan. The following MAbs may be used: FITC anti-HLA antibodies, -CD2 or mouse IgG1 irrelevant control, PE W6/32, anti-CD1a (Coulter), anti-CD4 or mouse IgG1 control (Becton Dickinson) and Tricolor (TC)-conjugated anti-CD45, -CD8, -CD3 or mouse IgG1 irrelevant control (Caltag).

Although the foregoing invention has been described in some detail by way of illustration and example for purposes of clarity of understanding, it will be apparent to those skilled in the art that certain changes and modifications may be practiced. Therefore, the description and examples should not be construed as limiting the scope of the invention, which is delineated by the appended claims.

We claim:

1. A method of obtaining a composition substantially enriched in a subpopulation of hematopoietic stem cells comprising:

obtaining a source of human hematopoietic cells;

separating a population of human hematopoietic cells from the source;

contacting the population of human hematopoietic cells with a monoclonal antibody specific for the marker CDw109; and separating the subpopulation that is specifically bound by the monoclonal antibody thereby obtaining a composition substantially enriched in a subpopulation of human hematopoietic stem cells.

2. The method according to claim 1, wherein the step of separating a population of human hematopoietic cells is by selecting for cells for expression of at least one additional marker associated with stem cells or by physical separation means.

3. The method according to claim 2 wherein the additional marker is selected from the group consisting of CD34, Thy-1 and rho.

4. A subpopulation of cells obtained by the method according to claim 3.

5. The method according to claim 2 further comprising the step of selecting for a cell lacking a lineage specific (Lin) marker.

6. The method according to claim 5 wherein the lineage specific marker is selected from the group consisting of CD2, CD14, CD15, CD16, CD19, and glycophorin A.

7. A subpopulation of cells obtained by the method according to claim 6.

8. A subpopulation of cells obtained by the method according to claim 5.

9. The method according to claim 1 wherein the step of separating a population of human hematopoietic cells is by selecting for a cell lacking a lineage specific (Lin)marker.

10. The method according to claim 9 wherein the lineage specific marker is selected from the group consisting of CD2, CD14, CD15, CD16, CD19, and glycophorin A.

11. A subpopulation of cells obtained by the method according to claim 9.

12. A subpopulation of cells obtained by the method according to claim 9.

13. A subpopulation of cells obtained by the method according to claim 1.

14. A method of obtaining a composition substantially enriched in a subpopulation of hematopoietic megakaryocyte progenitor cells comprising:

obtaining a source of hematopoietic cells;

separating a population of human hematopoietic cells from the source;

contacting a population of human hematopoietic cells with a monoclonal antibody specific for the marker CDw109: and separating the subpopulation that is specifically bound by the monoclonal antibody, thereby obtaining a composition substantially enriched in the subpopulation of human hematopoietic megakaryocyte progenitor cells.

15. The method according to claim 14 wherein the step of separating a population of human hematopoietic cells is by selecting for cells for expression of at least one additional marker associated with stem cells or by physical separation means.

16. The method according to claim 14 wherein the step of separating a population of human hematopoietic cells is by selecting for a cell lacking a lineage specific (Lin) marker.

17. A method for expanding hematopoietic megakaryocyte progenitor cells comprising:

obtaining a source of human hematopoietic cells:

separating a population of human hematopoietic cells from the source;

contacting the population of human hematopoietic cells with a monoclonal antibody specific for the marker CDw 109: and separating the subpopulation that is specifically bound by the monoclonal antibody; and culturing the subpopulation in the presence of an effective amount of at least one cytokine effective in inducing expansion of megakaryocyte progenitor cells, thereby expanding hematopoietic megakaryocyte progenitor cells.

18. The method according to claim 17 wherein the cytokine is Mp1 ligand.

19. The method according to claim 17 wherein the step of separating a population of human hematopoietic cells is by selecting for cells for expression of at least one additional marker associated with stem cells or by physical separation means.

20. The method according to claim 17 wherein the step of separating a population of human hematopoietic cells is by selecting for a cell lacking a lineage specific (Lin) marker.

21. A composition comprising hematopoietic cells enriched for megakaryocyte progenitor cells wherein the cells express CDw109 and CD34.

* * * * *

UNITED STATES PATENT AND TRADEMARK OFFICE
CERTIFICATE OF CORRECTION

PATENT NO. : 5,665,557
DATED : September 9, 1997
INVENTOR(S) : Lesley Murray and D. Robert Sutherland It is certified that error appears in the above-identified patent and that said Letters Patent is hereby corrected as shown below:

Column 18, Table 11, line 39, a line of text was missed. Please substitute for

"8A3        8A1        352"

the following:

--8A3        8A1        627
8A1        8A1        352--

Column 20, line 45 after the word "antibody" there should be --,--

Column 21, line 8 the number "9" should be --10--.

Signed and Sealed this

Tenth Day of March, 1998

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,665,557

DATED : September 9, 1997

INVENTOR(S) : Lesley Murray and D. Robert Sutherland

It is certified that error appears in the above-identified patent and that said Letters Patent is hereby corrected as shown below:

Column 18, Table 11, line 39, a line of text was missed. Please substitute for

"8A3        8A1        352"

the following:

--8A3        8A1        627
8A1        8A1        352--

Column 20, line 45 after the word "antibody" there should be --,--

Column 21, line 10, the number "9" should be --10--.

Signed and Sealed this

Seventh Day of April, 1998

Attest:

BRUCE LEHMAN

*Attesting Officer*        *Commissioner of Patents and Trademarks*